(12) United States Patent
Ho et al.

(10) Patent No.: US 11,037,464 B2
(45) Date of Patent: Jun. 15, 2021

(54) SYSTEM WITH EMULATOR MOVEMENT TRACKING FOR CONTROLLING MEDICAL DEVICES

(71) Applicant: Auris Health, Inc., Redwood City, CA (US)

(72) Inventors: Michael Shyh-Yen Ho, San Francisco, CA (US); David S. Mintz, Mountain View, CA (US); Edward Joseph Menard, San Carlos, CA (US); Mark A. Lown, Union City, CA (US); Jason Tomas Wilson, Redwood City, CA (US); Yanan Huang, Foster City, CA (US)

(73) Assignee: Auris Health, Inc., Redwood City, CA (US)

( * ) Notice: Subject to any disclaimer, the term of this patent is extended or adjusted under 35 U.S.C. 154(b) by 345 days.

(21) Appl. No.: 15/657,051

(22) Filed: Jul. 21, 2017

(65) Prior Publication Data
US 2018/0025666 A1      Jan. 25, 2018

Related U.S. Application Data

(60) Provisional application No. 62/365,308, filed on Jul. 21, 2016.

(51) Int. Cl.
*G06F 17/00*      (2019.01)
*G09B 23/28*      (2006.01)
(Continued)

(52) U.S. Cl.
CPC .............. *G09B 23/28* (2013.01); *A61B 34/35* (2016.02); *G09B 5/02* (2013.01); *G09B 9/00* (2013.01)

(58) Field of Classification Search
CPC .. G09B 23/28; G09B 5/02; G09B 9/00; A61B 34/35
(Continued)

(56) References Cited

U.S. PATENT DOCUMENTS 4,771,262 A    9/1988   Reuss
4,896,554 A    1/1990   Culver
(Continued)

FOREIGN PATENT DOCUMENTS

EP      1 800 593      6/2007
EP      1 109 497      5/2009
(Continued)

*Primary Examiner* — Ronnie M Mancho
(74) *Attorney, Agent, or Firm* — Morgan, Lewis & Bocklus LLP

(57) ABSTRACT

The systems and methods disclosed herein are directed to robotically controlling a medical device to utilize manual skills and techniques developed by surgeons. The system may comprise an emulator representing a medical device. The system may comprise at least one detector configured to track the emulator. The system may further comprise an imaging device configured to track the medical device. The system may be configured to move the medical device to reduce an alignment offset between the location of the emulator and the location of the medical device, to move the imaging device based on the translational movement of the emulator, and/or to move the medical device based on data indicative of an orientation of the emulator.

20 Claims, 15 Drawing Sheets

(51) Int. Cl.
*G09B 5/02* (2006.01)
*G09B 9/00* (2006.01)
*A61B 34/35* (2016.01)

(58) Field of Classification Search
USPC ........................................................ 700/245
See application file for complete search history.

(56) References Cited

U.S. PATENT DOCUMENTS

| | | | |
|---|---|---|---|
| 5,008,528 A | 4/1991 | Duchon | |
| 5,176,310 A | 1/1993 | Akiyama et al. | |
| 5,280,781 A | 1/1994 | Oku | |
| 5,499,632 A | 3/1996 | Hill et al. | |
| 5,524,180 A | 6/1996 | Wang et al. | |
| 5,526,812 A | 6/1996 | Dumoulin et al. | |
| 5,762,458 A | 6/1998 | Wang et al. | |
| 5,831,614 A | 11/1998 | Tognazzini et al. | |
| 5,899,851 A | 5/1999 | Koninckx | |
| 5,963,770 A | 10/1999 | Eakin | |
| 6,007,550 A | 12/1999 | Wang et al. | |
| 6,016,439 A | 1/2000 | Acker | |
| 6,038,467 A | 3/2000 | De Bliek et al. | |
| 6,096,004 A | 8/2000 | Meglan et al. | |
| 6,425,865 B1 | 7/2002 | Salcudean et al. | |
| 6,466,198 B1 | 10/2002 | Feinstein | |
| 6,468,265 B1* | 10/2002 | Evans ................... | A61B 34/32 600/103 |
| 6,490,467 B1 | 12/2002 | Bucholz | |
| 6,516,421 B1 | 2/2003 | Peters | |
| 6,690,964 B2 | 2/2004 | Beiger et al. | |
| 6,856,827 B2 | 2/2005 | Seeley et al. | |
| 7,206,627 B2 | 4/2007 | Abovitz | |
| 7,594,925 B2 | 9/2009 | Danek | |
| 8,180,114 B2 | 5/2012 | Nishihara et al. | |
| 8,716,973 B1 | 5/2014 | Lammertse | |
| 8,718,837 B2* | 5/2014 | Wang ..................... | B25J 9/1689 701/2 |
| 8,971,597 B2* | 3/2015 | Zhao ...................... | A61B 34/30 382/128 |
| 9,241,767 B2 | 1/2016 | Prisco et al. | |
| 9,283,046 B2 | 3/2016 | Walker et al. | |
| 9,498,291 B2 | 11/2016 | Balaji et al. | |
| 9,503,681 B1* | 11/2016 | Popescu ................ | G06T 19/006 |
| 9,504,604 B2 | 11/2016 | Alvarez | |
| 9,561,019 B2* | 2/2017 | Mihailescu ............ | A61B 5/064 |
| 9,561,083 B2 | 2/2017 | Yu et al. | |
| 9,566,414 B2 | 2/2017 | Wong et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,770,216 B2 | 9/2017 | Brown et al. | |
| 9,788,910 B2 | 10/2017 | Schuh | |
| 9,818,681 B2 | 11/2017 | Machida | |
| 9,827,061 B2 | 11/2017 | Balaji et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 10,016,900 B1 | 7/2018 | Meyer et al. | |
| 10,022,192 B1 | 7/2018 | Ummalaneni | |
| 10,028,789 B2 | 7/2018 | Quaid et al. | |
| 10,130,427 B2* | 11/2018 | Tanner ................... | A61B 6/12 |
| 10,136,959 B2 | 11/2018 | Mintz et al. | |
| 10,145,747 B1 | 12/2018 | Lin et al. | |
| 10,159,532 B1 | 12/2018 | Ummalaneni et al. | |
| 10,231,793 B2 | 3/2019 | Romo | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,346,976 B2 | 7/2019 | Averbuch | |
| 10,426,559 B2 | 10/2019 | Graetzel et al. | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,517,692 B2 | 12/2019 | Eyre et al. | |
| 10,524,866 B2 | 1/2020 | Srinivasan | |
| 10,639,114 B2 | 5/2020 | Schuh | |
| 10,667,875 B2 | 6/2020 | DeFonzo | |
| 10,743,751 B2 | 8/2020 | Landey et al. | |
| 10,751,140 B2 | 8/2020 | Wallace et al. | |
| 10,765,487 B2 | 9/2020 | Ho | |
| 10,779,898 B2 | 9/2020 | Hill | |
| 10,814,101 B2 | 10/2020 | Jiang | |
| 10,820,947 B2 | 11/2020 | Julian | |
| 10,820,954 B2 | 11/2020 | Marsot et al. | |
| 10,828,118 B2 | 11/2020 | Schuh et al. | |
| 2002/0077533 A1 | 6/2002 | Bieger et al. | |
| 2002/0082612 A1 | 6/2002 | Moll et al. | |
| 2002/0120188 A1 | 8/2002 | Brock et al. | |
| 2002/0161280 A1 | 10/2002 | Chatenever et al. | |
| 2002/0173878 A1 | 11/2002 | Watanabe | |
| 2004/0047044 A1 | 3/2004 | Dalton | |
| 2004/0263535 A1 | 12/2004 | Birkenbach et al. | |
| 2005/0043718 A1 | 2/2005 | Madhani | |
| 2005/0085714 A1 | 4/2005 | Foley et al. | |
| 2005/0193451 A1 | 9/2005 | Quistgaard et al. | |
| 2005/0222554 A1 | 10/2005 | Wallace et al. | |
| 2006/0079745 A1 | 4/2006 | Viswanathan et al. | |
| 2006/0095022 A1 | 5/2006 | Moll et al. | |
| 2006/0173290 A1 | 8/2006 | Lavallee et al. | |
| 2006/0200026 A1 | 9/2006 | Wallace et al. | |
| 2007/0083098 A1* | 4/2007 | Stern ..................... | A61B 1/00188 600/407 |
| 2007/0138992 A1 | 6/2007 | Prisco et al. | |
| 2007/0144298 A1 | 6/2007 | Miller | |
| 2007/0185486 A1 | 8/2007 | Hauck et al. | |
| 2008/0027313 A1 | 1/2008 | Shachar | |
| 2008/0033442 A1 | 2/2008 | Amoit | |
| 2008/0082109 A1 | 4/2008 | Moll et al. | |
| 2008/0097465 A1 | 4/2008 | Rollins et al. | |
| 2008/0108870 A1 | 5/2008 | Wiita et al. | |
| 2008/0140087 A1 | 6/2008 | Barbagli et al. | |
| 2008/0159653 A1 | 7/2008 | Dunki-Jacobs et al. | |
| 2008/0183068 A1 | 7/2008 | Carls et al. | |
| 2008/0183188 A1 | 7/2008 | Carls et al. | |
| 2008/0306490 A1 | 12/2008 | Lakin et al. | |
| 2009/0248036 A1 | 10/2009 | Hoffman et al. | |
| 2009/0259230 A1 | 10/2009 | Khadem | |
| 2009/0326322 A1 | 12/2009 | Diolaiti | |
| 2009/0326556 A1 | 12/2009 | Diolaiti et al. | |
| 2010/0019890 A1 | 1/2010 | Helmer et al. | |
| 2010/0039506 A1 | 2/2010 | Sarvestani et al. | |
| 2010/0076263 A1 | 3/2010 | Tanaka | |
| 2010/0121269 A1 | 5/2010 | Goldenberg | |
| 2010/0125284 A1 | 5/2010 | Tanner et al. | |
| 2010/0161129 A1 | 6/2010 | Costa et al. | |
| 2010/0204613 A1 | 8/2010 | Rollins et al. | |
| 2010/0225209 A1* | 9/2010 | Goldberg .............. | A61B 34/30 312/209 |
| 2010/0328455 A1 | 12/2010 | Nam et al. | |
| 2011/0021926 A1 | 1/2011 | Spencer | |
| 2011/0113852 A1 | 5/2011 | Prisco | |
| 2011/0118748 A1* | 5/2011 | Itkowitz ................ | A61B 34/30 606/130 |
| 2011/0118752 A1* | 5/2011 | Itkowitz ................ | B25J 9/1689 606/130 |
| 2011/0118753 A1* | 5/2011 | Itkowitz ................ | G06F 3/014 606/130 |
| 2011/0130718 A1 | 6/2011 | Kidd et al. | |
| 2011/0196199 A1 | 8/2011 | Donhowe et al. | |
| 2011/0235855 A1 | 9/2011 | Smith | |
| 2011/0238010 A1 | 9/2011 | Kirschenman et al. | |
| 2011/0248987 A1 | 10/2011 | Mitchell | |
| 2011/0276058 A1 | 11/2011 | Choi et al. | |
| 2011/0306873 A1* | 12/2011 | Shenai .................. | A61B 8/0841 600/424 |
| 2012/0059392 A1 | 3/2012 | Diolaiti | |

(56) References Cited

U.S. PATENT DOCUMENTS

| | | | |
|---|---|---|---|
| 2012/0071752 A1* | 3/2012 | Sewell | A61B 6/12 600/424 |
| 2012/0071891 A1* | 3/2012 | Itkowitz | B25J 13/084 606/130 |
| 2012/0071892 A1* | 3/2012 | Itkowitz | B25J 13/086 606/130 |
| 2012/0071894 A1 | 3/2012 | Tanner et al. | |
| 2012/0075638 A1 | 3/2012 | Rollins et al. | |
| 2012/0078053 A1* | 3/2012 | Phee | A61B 1/00147 600/139 |
| 2012/0103123 A1 | 5/2012 | McInroy et al. | |
| 2012/0158011 A1 | 6/2012 | Sandhu | |
| 2012/0203067 A1 | 8/2012 | Higgins et al. | |
| 2012/0253276 A1 | 10/2012 | Govari et al. | |
| 2012/0296161 A1 | 11/2012 | Wallace et al. | |
| 2012/0314022 A1 | 12/2012 | Jo | |
| 2013/0018306 A1 | 1/2013 | Ludwin | |
| 2013/0060146 A1 | 3/2013 | Yang et al. | |
| 2013/0165854 A1 | 6/2013 | Sandhu et al. | |
| 2013/0245375 A1 | 9/2013 | DiMaio et al. | |
| 2013/0317519 A1 | 11/2013 | Romo et al. | |
| 2014/0107666 A1 | 4/2014 | Madhani | |
| 2014/0111457 A1 | 4/2014 | Briden et al. | |
| 2014/0142591 A1 | 5/2014 | Alvarez et al. | |
| 2014/0222204 A1 | 8/2014 | Kawashima | |
| 2014/0276392 A1 | 9/2014 | Wong et al. | |
| 2014/0276938 A1 | 9/2014 | Hsu et al. | |
| 2014/0277333 A1 | 9/2014 | Lewis et al. | |
| 2014/0309649 A1 | 10/2014 | Alvarez et al. | |
| 2014/0357984 A1 | 12/2014 | Wallace et al. | |
| 2014/0364870 A1 | 12/2014 | Alvarez et al. | |
| 2014/0379000 A1 | 12/2014 | Romo et al. | |
| 2015/0018622 A1* | 1/2015 | Tesar | A61B 1/05 600/202 |
| 2015/0051592 A1 | 2/2015 | Kintz | |
| 2015/0101442 A1 | 4/2015 | Romo | |
| 2015/0105747 A1 | 4/2015 | Rollins et al. | |
| 2015/0119638 A1 | 4/2015 | Yu et al. | |
| 2015/0157191 A1* | 6/2015 | Phee | B25J 9/1674 600/106 |
| 2015/0164594 A1 | 6/2015 | Romo et al. | |
| 2015/0164596 A1 | 6/2015 | Romo | |
| 2015/0224845 A1* | 8/2015 | Anderson | B60G 17/019 701/37 |
| 2015/0265807 A1 | 9/2015 | Park et al. | |
| 2015/0290454 A1* | 10/2015 | Tyler | A61N 1/0548 607/134 |
| 2015/0335480 A1 | 11/2015 | Alvarez et al. | |
| 2015/0375399 A1 | 12/2015 | Chiu et al. | |
| 2016/0001038 A1 | 1/2016 | Romo et al. | |
| 2016/0026253 A1* | 1/2016 | Bradski | G02B 27/225 345/8 |
| 2016/0059412 A1* | 3/2016 | Oleynik | B25J 9/163 700/257 |
| 2016/0098095 A1* | 4/2016 | Gonzalez-Banos | G06F 3/017 345/156 |
| 2016/0175059 A1 | 6/2016 | Walker et al. | |
| 2016/0183841 A1 | 6/2016 | Duindam et al. | |
| 2016/0213436 A1* | 7/2016 | Inoue | A61B 17/3421 |
| 2016/0213884 A1 | 7/2016 | Park | |
| 2016/0256069 A1 | 9/2016 | Jenkins | |
| 2016/0270865 A1 | 9/2016 | Landey et al. | |
| 2016/0287279 A1 | 10/2016 | Bovay et al. | |
| 2016/0296294 A1 | 10/2016 | Moll et al. | |
| 2016/0314710 A1* | 10/2016 | Jarc | G09B 23/285 |
| 2016/0314716 A1* | 10/2016 | Grubbs | G09B 23/28 |
| 2016/0314717 A1* | 10/2016 | Grubbs | G09B 23/306 |
| 2016/0324580 A1 | 11/2016 | Esterberg et al. | |
| 2016/0374541 A1 | 12/2016 | Agrawal et al. | |
| 2017/0007337 A1 | 1/2017 | Dan | |
| 2017/0065364 A1 | 3/2017 | Schuh et al. | |
| 2017/0065365 A1 | 3/2017 | Schuh | |
| 2017/0100199 A1 | 4/2017 | Yu et al. | |
| 2017/0105803 A1 | 4/2017 | Wong et al. | |
| 2017/0113019 A1 | 4/2017 | Wong et al. | |
| 2017/0119411 A1 | 5/2017 | Shah | |
| 2017/0119412 A1 | 5/2017 | Noonan et al. | |
| 2017/0119413 A1 | 5/2017 | Romo | |
| 2017/0119481 A1 | 5/2017 | Romo et al. | |
| 2017/0143429 A1* | 5/2017 | Richmond | A61B 5/064 |
| 2017/0165011 A1 | 6/2017 | Bovay et al. | |
| 2017/0172664 A1 | 6/2017 | Weingarten et al. | |
| 2017/0172673 A1 | 6/2017 | Yu et al. | |
| 2017/0202627 A1 | 7/2017 | Sramek et al. | |
| 2017/0209073 A1 | 7/2017 | Sramek et al. | |
| 2017/0290631 A1 | 10/2017 | Lee et al. | |
| 2017/0333679 A1 | 11/2017 | Jiang | |
| 2017/0340396 A1 | 11/2017 | Romo et al. | |
| 2017/0365055 A1 | 12/2017 | Mintz et al. | |
| 2017/0367782 A1 | 12/2017 | Schuh et al. | |
| 2018/0055583 A1 | 3/2018 | Schuh et al. | |
| 2018/0078321 A1* | 3/2018 | Liao | A61B 90/361 |
| 2018/0079090 A1 | 3/2018 | Koenig et al. | |
| 2018/0177556 A1 | 6/2018 | Noonan et al. | |
| 2018/0214011 A1 | 8/2018 | Graetzel et al. | |
| 2018/0221038 A1 | 8/2018 | Noonan et al. | |
| 2018/0221039 A1 | 8/2018 | Shah | |
| 2018/0250083 A1 | 9/2018 | Schuh et al. | |
| 2018/0271616 A1 | 9/2018 | Schuh et al. | |
| 2018/0279852 A1 | 10/2018 | Rafii-Tari et al. | |
| 2018/0280660 A1 | 10/2018 | Landey et al. | |
| 2018/0289431 A1 | 10/2018 | Draper et al. | |
| 2018/0325499 A1 | 11/2018 | Landey et al. | |
| 2018/0333044 A1 | 11/2018 | Jenkins | |
| 2018/0360435 A1 | 12/2018 | Romo | |
| 2019/0000559 A1 | 1/2019 | Berman et al. | |
| 2019/0000560 A1 | 1/2019 | Berman et al. | |
| 2019/0000576 A1 | 1/2019 | Mintz et al. | |
| 2019/0083183 A1 | 3/2019 | Moll et al. | |
| 2019/0090969 A1* | 3/2019 | Jarc | A61B 90/00 |
| 2019/0105776 A1 | 4/2019 | Ho et al. | |
| 2019/0107454 A1 | 4/2019 | Lin | |
| 2019/0110839 A1 | 4/2019 | Rafii-Tari et al. | |
| 2019/0110843 A1 | 4/2019 | Ummalaneni et al. | |
| 2019/0151148 A1 | 4/2019 | Alvarez et al. | |
| 2019/0151032 A1* | 5/2019 | Mustufa | A61B 90/37 |
| 2019/0167361 A1 | 6/2019 | Walker et al. | |
| 2019/0167366 A1 | 6/2019 | Ummalaneni | |
| 2019/0175009 A1 | 6/2019 | Mintz | |
| 2019/0175062 A1 | 6/2019 | Rafii-Tari et al. | |
| 2019/0175287 A1 | 6/2019 | Hill | |
| 2019/0175799 A1 | 6/2019 | Hsu | |
| 2019/0183585 A1 | 6/2019 | Rafii-Tari et al. | |
| 2019/0183587 A1 | 6/2019 | Rafii-Tari et al. | |
| 2019/0216548 A1 | 7/2019 | Ummalaneni | |
| 2019/0216550 A1 | 7/2019 | Eyre | |
| 2019/0216576 A1 | 7/2019 | Eyre | |
| 2019/0223974 A1 | 7/2019 | Romo | |
| 2019/0228525 A1 | 7/2019 | Mintz et al. | |
| 2019/0228528 A1 | 7/2019 | Mintz et al. | |
| 2019/0246882 A1 | 8/2019 | Graetzel et al. | |
| 2019/0262086 A1 | 8/2019 | Connolly et al. | |
| 2019/0269468 A1 | 9/2019 | Hsu et al. | |
| 2019/0274764 A1 | 9/2019 | Romo | |
| 2019/0290109 A1 | 9/2019 | Agrawal et al. | |
| 2019/0298160 A1 | 10/2019 | Ummalaneni et al. | |
| 2019/0298458 A1 | 10/2019 | Srinivasan | |
| 2019/0298460 A1 | 10/2019 | Al-Jadda | |
| 2019/0298465 A1 | 10/2019 | Chin | |
| 2019/0328213 A1 | 10/2019 | Landey et al. | |
| 2019/0336238 A1 | 11/2019 | Yu | |
| 2019/0365201 A1 | 12/2019 | Noonan et al. | |
| 2019/0365209 A1 | 12/2019 | Ye et al. | |
| 2019/0365479 A1 | 12/2019 | Rafii-Tari | |
| 2019/0365486 A1 | 12/2019 | Srinivasan et al. | |
| 2019/0371012 A1 | 12/2019 | Flexman | |
| 2019/0374297 A1 | 12/2019 | Wallace et al. | |
| 2019/0375383 A1 | 12/2019 | Alvarez | |
| 2019/0380787 A1 | 12/2019 | Ye | |
| 2019/0380797 A1 | 12/2019 | Yu | |
| 2020/0000533 A1 | 1/2020 | Schuh | |
| 2020/0022767 A1 | 1/2020 | Hill | |
| 2020/0038123 A1 | 2/2020 | Graetzel | |

(56) References Cited

U.S. PATENT DOCUMENTS

| | | |
|---|---|---|
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0345432 A1 | 11/2020 | Walker |
| 2020/0352420 A1 | 11/2020 | Graetzel |
| 2020/0360183 A1 | 11/2020 | Alvarez |
| 2020/0360659 A1 | 11/2020 | Wong |
| 2020/0367726 A1 | 11/2020 | Landey et al. |
| 2020/0367981 A1 | 11/2020 | Ho et al. |
| 2020/0375678 A1 | 12/2020 | Wallace |

FOREIGN PATENT DOCUMENTS

| | | |
|---|---|---|
| EP | 2 158 834 | 3/2010 |
| WO | WO 08/049088 | 4/2008 |
| WO | WO 10/025522 | 3/2010 |
| WO | WO 17/214243 | 12/2017 |

\* cited by examiner

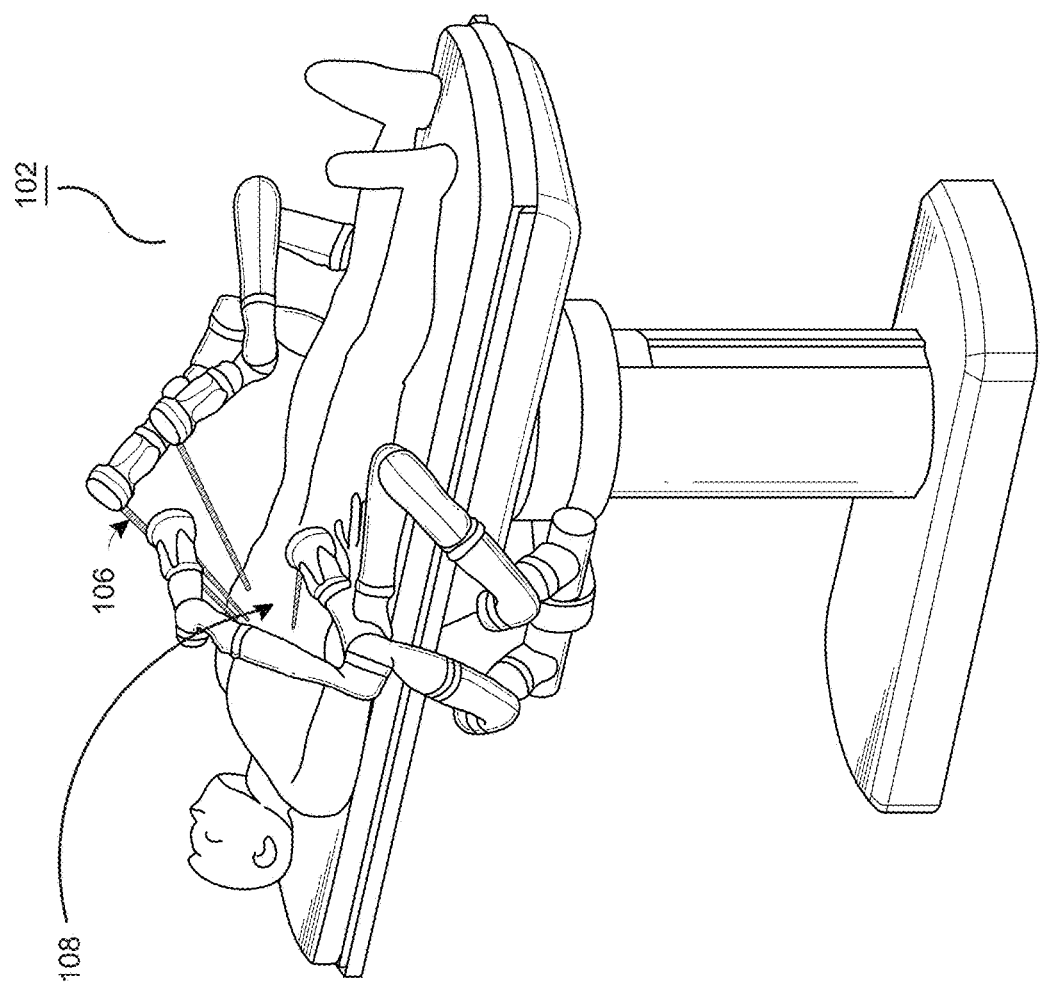
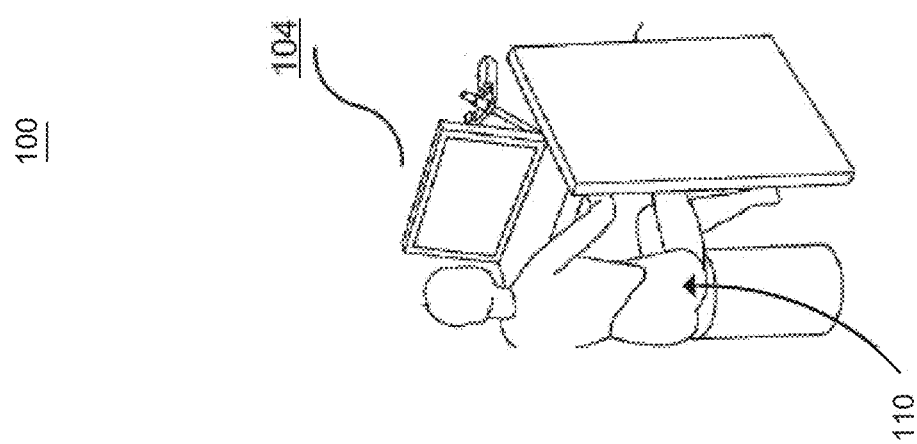
FIG. 1

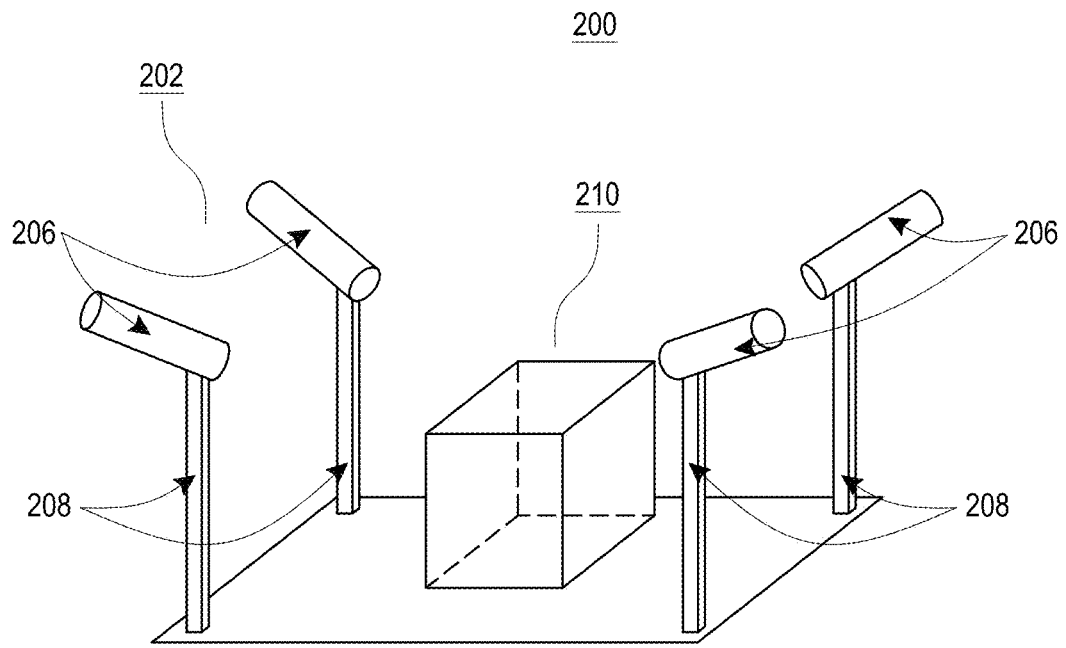
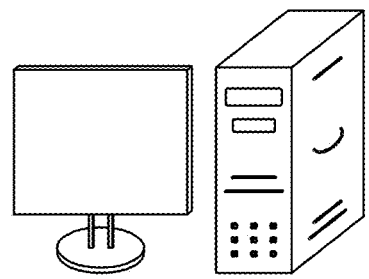
FIG. 2

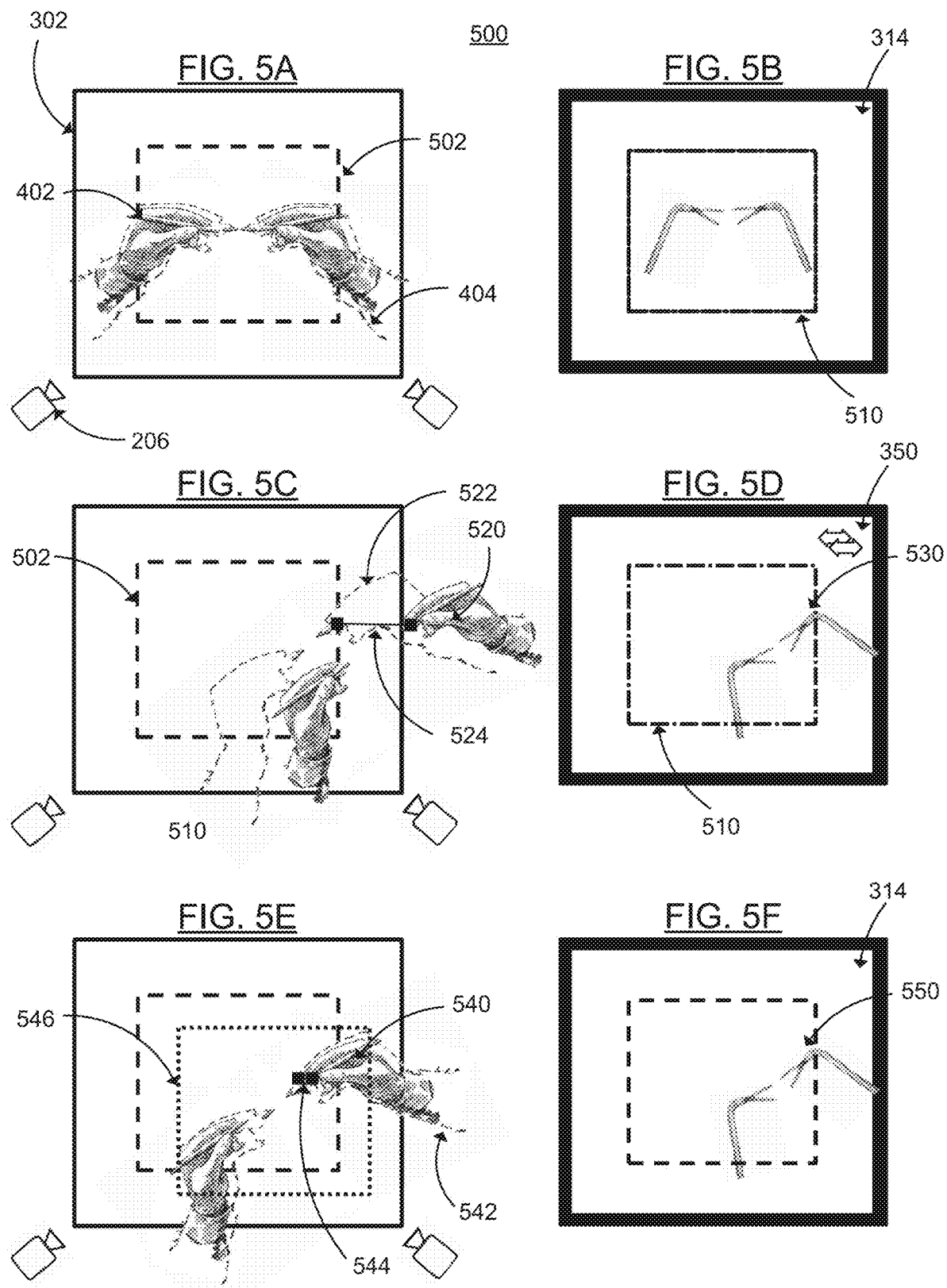

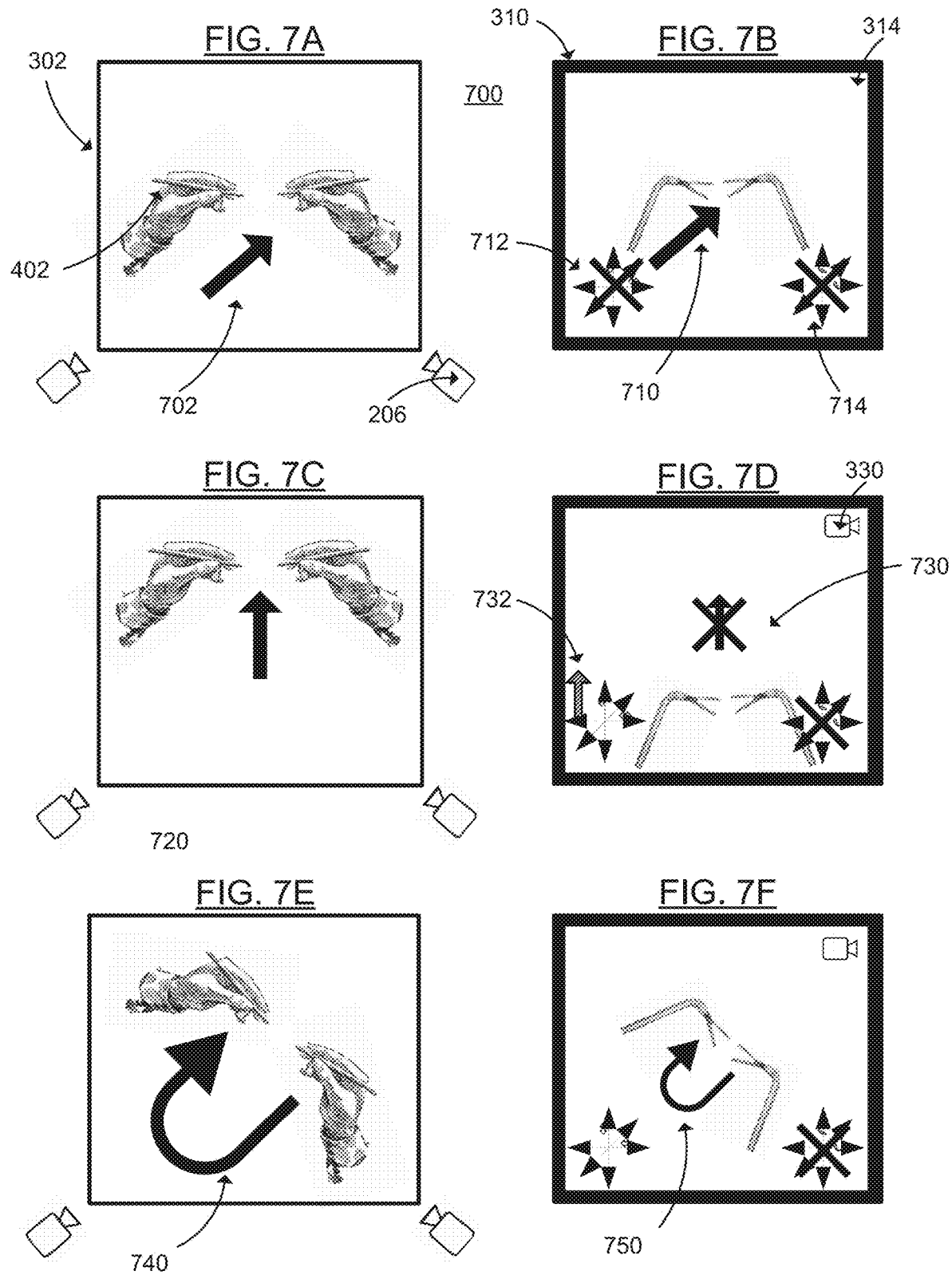

$$\phi_1 = f(\lambda_1, \omega_1, \alpha_1)$$

$$\phi_2 = f(\lambda_2, \omega_2, \alpha_2)$$

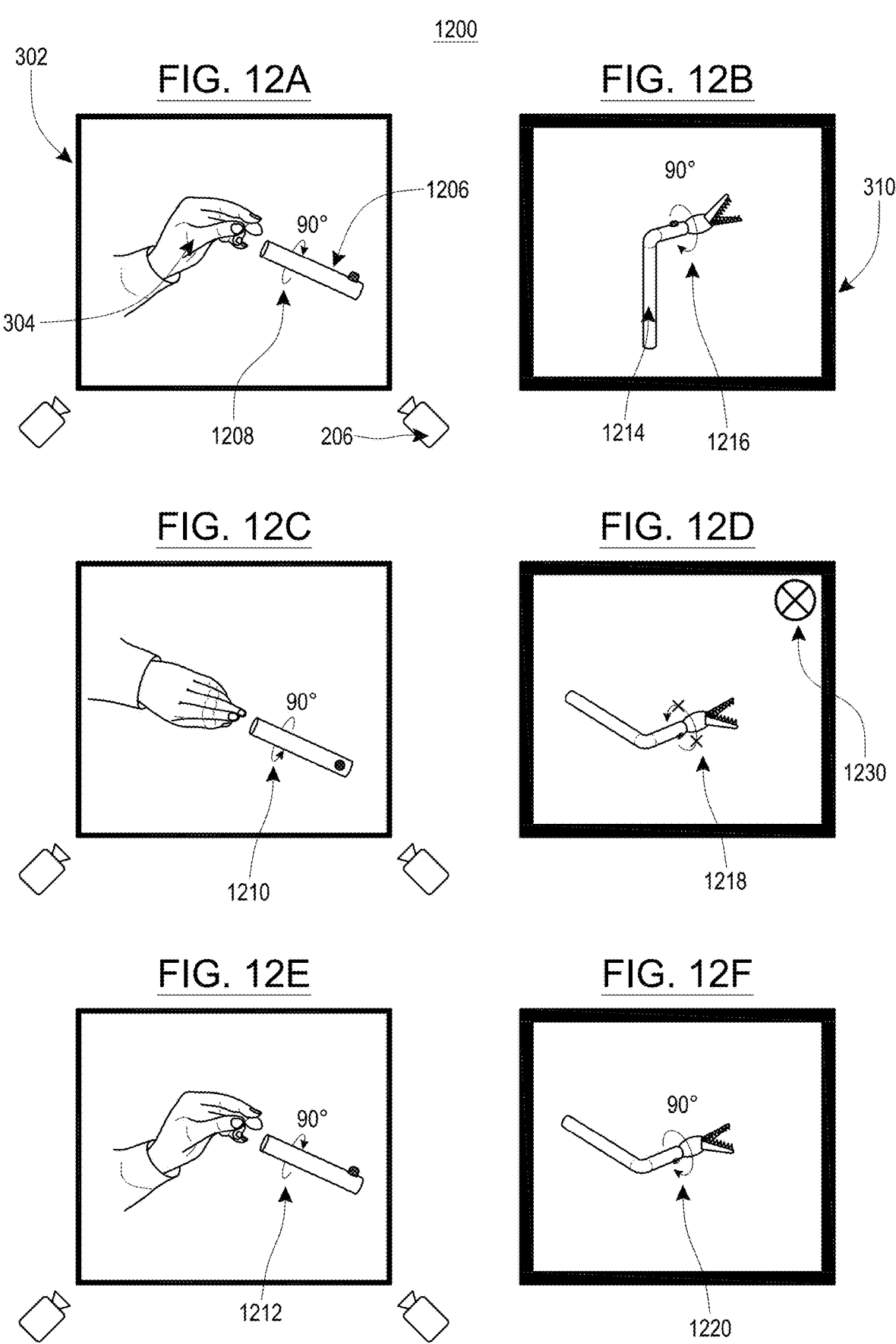

SYSTEM WITH EMULATOR MOVEMENT TRACKING FOR CONTROLLING MEDICAL DEVICES

BACKGROUND

The use of robotic medical technologies presents a number of advantages over traditional, manual medical procedures (e.g., surgery). Robotic surgeries allow for higher degree of precision, control, and access among many other advantages. Despite these advantages and recent improvements in the technology, many existing robotic surgical platforms are limited by their user interfaces. A great majority of surgical robotic interfaces comprise joysticks or other mechanical devices mounted to an instrument that is manipulated by an operator (e.g., the surgeon) to control the tools performing surgery on the patient. Most of these interfaces are not intuitive nor are they designed to mimic the surgical motions and skills that surgeons have spent a multitude of hours training and honing. Generally, the direct manipulation of robotic elements via the mechanical interface requires a separate training regimen forcing the physician to learn new skills rather than employing techniques developed over many years.

An additional problem to robotic joystick systems is that the haptic feedback of a robotic system is not a similar representation of the haptic feedback received from traditional surgical tools. In a typical procedure, surgical tools have a specific weight, feel, and ease of motion. In robotic procedures, the joystick system is engineered to try and mimic these characteristics but prove lacking in many instances, e.g. a mounted joystick with actuators is not able to have the same ease of movement and degree of freedom as a hand holding a scalpel. This inconsistency forces the operator to develop a separate set of responses for the haptic feedback cues received from the joystick system, complicating the transition to a robotic system.

For these reasons, it would be desirable to provide additional and alternative user interfaces for the performance of robotically assisted medical, surgical, and diagnostic procedures. Such interfaces and methods for their use should allow physicians to manipulate tools in a manner that more closely mimics the use of conventional tools in non-robotic medical or surgical procedures.

SUMMARY

The systems, methods and devices of this disclosure each have several innovative aspects, no single one of which is solely responsible for the desirable attributes disclosed herein.

One aspect relates to a system, comprising: an emulator configured to be held and operated in a free working space (FWS), the emulator representing a medical device at a target site; at least one detector configured to track the emulator within the FWS; at least one computer-readable memory having stored thereon executable instructions; and at least one processor in communication with the at least one computer-readable memory and configured to execute the instructions to cause the system to: determine an alignment offset between a location of the emulator and a location of the medical device; during a medical procedure, determine a first movement amount based on a signal from the at least one detector indicative of a first movement of the emulator within the FWS; adjust the first movement amount by a first adjustment value; and generate instructions to move the medical device based on the adjusted first movement amount, wherein movement of the medical device by the adjusted first movement amount reduces the alignment offset between the location of the emulator and the location of the medical device.

In some implementations, the at least one processor is configured to execute the instructions to cause the system to: during the medical procedure, determine a second movement amount based on a signal from the at least one detector indicative of a second movement of the emulator within the FWS; adjust the second movement amount by a second adjustment value; and generate instructions to move the medical device based on the adjusted second movement amount, wherein movement of the medical device by the adjusted second movement amount reduces the alignment offset between the location of the emulator and the location of the medical device.

In some implementations, the movement of the medical device by the adjusted first and second movement amounts eliminates the alignment offset between the location of the emulator and the location of the medical device.

Another aspect relates to a system, comprising: an emulator configured to be held and operated in a FWS, the emulator representing a medical device at a target site; at least one detector configured to track the emulator within the FWS; an imaging device configured to track the medical device at the target site; at least one computer-readable memory having stored thereon executable instructions; and at least one processor in communication with the at least one computer-readable memory and configured to execute the instructions to cause the system to: receive a signal from the at least one detector indicative of a translational movement of the emulator within the FWS; and generate instructions, based on the translational movement of the emulator, to move the imaging device within a plane defined by pitch and yaw axes of the imaging device.

In some implementations, the translational movement of the emulator does not result in a translational movement of the medical device. In some implementations, the at least one processor is configured to execute the instructions to cause the system to: receive a signal from the at least one detector indicative of a rotational movement of the emulator within the FWS; and generate instructions, based on the rotational movement of the emulator, to rotate the medical device along a roll axis of the medical device. In some implementations, the rotational movement of the emulator does not result in a rotational movement of the imaging device.

Yet another aspect relates to a system, comprising: an emulator representing a medical device at a target site; a first set of one or more detectors configured to track the emulator; a second set of one or more detectors configured to track the medical device at the target site; at least one computer-readable memory having stored thereon executable instructions; and at least one processor in communication with the at least one computer-readable memory and configured to execute the instructions to cause the system to: receive, from the first set of one or more detectors, first data indicative of at least an orientation of the emulator, the first data comprising roll data, pitch data, and yaw data of the emulator; generate, based on a clutched user input, instructions to move the medical device based on the first data discounting the roll data of the emulator; and cause the medical device to move based on the instructions.

In some implementations, the emulator is configured to be held and operated in a FWS; and the first set of one or more detectors is configured to track motion of the emulator in the FWS. In some implementations, the emulator comprises a mechanical emulator; and the first set of one or more detectors is configured to track mechanical movement of the emulator.

In some implementations, the discounting of the roll data of the emulator is based on decoupling a roll axis of the emulator from yaw and pitch axes of the emulator. In some implementations, the discounting of the roll data of the emulator is based on decoupling an absolute roll angle of the medical device from an absolute roll angle of the emulator.

In some implementations, the emulator is symmetric with respect to a roll axis of the emulator. In other implementations, the emulator is asymmetric with respect to a roll axis of the emulator.

In some implementations, the movement of the medical device based on the instructions facilitates adjustment of a roll axis of the emulator with respect to a roll axis of the medical device. In some implementations, the at least one processor is configured to execute the instructions to cause the system to receive, from the second set of one or more detectors, second data indicative of an orientation of the medical device at the target site, the second data comprising roll data, pitch data, and yaw data of the medical device; and the alignment of the respective roll axes of the emulator and the medical device is based on the pitch and yaw data of the emulator and the pitch and yaw data of the medical device.

In some implementations, the at least one processor is configured to execute the instructions to cause the system to: receive, from the first set of one or more detectors, third data indicative of a translational movement of the emulator; receive, from the second set of one or more detectors, fourth data indicative of a position of the medical device at the target site; and generate instructions to move the medical device based on the third and fourth data.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIG. 1 illustrates an embodiment of a master/slave surgical tool system for minimally invasive surgery, the master device employing joysticks for manipulating the slave surgical tools.

FIG. 2 illustrates an embodiment of a three-dimensional motion tracking system.

FIG. 5A illustrates the free working space of a master/slave surgical system operating in active mode without relative misalignment and with the emulators within the limited working area, according to one embodiment.

FIG. 5B illustrates the video display during active mode operation when the effectors remain within the limited working area, according to one embodiment.

FIG. 5C illustrates a situation within the free working space of a master/slave surgical system triggering alignment mode operation due to motion of the emulators near the boundaries of the representative limited working area causing relative misalignment, according to one embodiment.

FIG. 5D illustrates the video display during alignment mode operation when the effectors are at the boundaries of the limited working area, according to one embodiment.

FIG. 5E illustrates a situation within the free working space of a master/slave surgical system reentering active mode operation due to realignment of the position of the emulators and the position of the representative effectors, according to one embodiment.

FIG. 5F illustrates the video display during active mode operation due to realignment of the position of the emulators and the position of the representative effectors, according to one embodiment.

FIG. 7A illustrates translational movement of the emulators within the free working space for control of the surgical effectors at the surgical site while the master/slave surgical system is operating in active mode, according to one embodiment.

FIG. 7B illustrates translational movement of the effectors resulting from translational movement of the emulators displayed on the video screen while the master/slave surgical system is operating in active mode, according to one embodiment.

FIG. 7C illustrates translational movement of the emulators within the free working space for control of the camera at the surgical site while the master/slave surgical system is operating in camera mode, according to one embodiment.

FIG. 7D illustrates translational movement of the camera resulting from translational movement of the emulators displayed on the video screen while the master/slave surgical system is operating in camera mode, according to one embodiment.

FIG. 7E illustrates rotational movement of the emulators within the free working space for control of the effectors at the surgical site while the master/slave surgical system is operating in camera mode, according to one embodiment.

FIG. 7F illustrates rotational movement of the effectors resulting from rotational movement of the emulators displayed on the video screen while the master/slave surgical system is operating in camera mode, according to one embodiment.

FIGS. 12A-12F illustrate an emulator and a representative medical device during a clutched roll process, according to one embodiment.

DETAILED DESCRIPTION

Figure 3A:
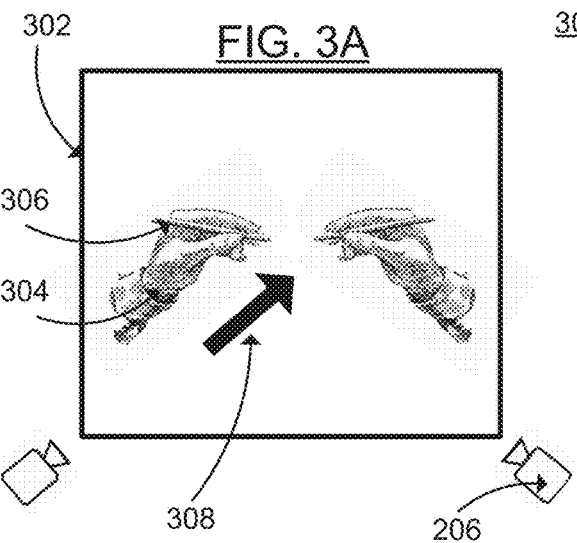
FIG. 3A illustrates an embodiment of master device movement within the free working space while the master/slave surgical system is in active mode.

This description presents a method for robotically controlling medical devices (e.g., surgical effectors, tools, devices, or instruments) at a target site (e.g., a surgical site) that utilizes the highly specialized manual skills and techniques developed by surgeons over time. Specifically, a motion tracking system that directly translates the motion of hand(s) of an operator (e.g., a surgeon) in free space to motions of a robotic surgical effector at the surgical site. The system tracking, interpreting, and translating the position and actions of the surgeon creates a more characteristic experience for the operator. Thus, the presented robotic surgical system yields a more natural transition towards advanced robotic techniques for surgical operations from the widely used manual techniques.

Additionally, the system includes an emulator held by the operator and operated in a free working space (FWS), the emulator representing a corresponding medical device at the target site. The emulator design closely mimics the corresponding medical device at the target site in weight, range of motion, and functional abilities, e.g. the surgeon holding surgical scissor emulators is controlling surgical scissors at the target site. The system may comprise at least one detector configured to track the emulator within the FWS and/or at least one detector (e.g., imaging device) configured to track the medical device at the target site. The detector may comprise one or more components of electromechanical systems such as, for example, encoders, potentiometers, linear variable differential transformers (LVDT), and rotary variable differential transformers (RVDT).

The description below contains the following sections:

Section I: Describes an overview of a conventional master/slave robotic surgical process.

Section II: Describes an example of a three-dimensional motion tracking system for controlling slave surgical effectors at the surgery site.

Section III: Describes the operative modes of a master/slave surgical system.

Section IV: Describes a haptic response to indicate master/slave alignment.

Section V: Describes a system for handling motion of the master device that would create motion of the slave device outside of its possible range of motion.

Section VI: Describes an emulator for detecting the operator's grip on the emulators.

Section VII: Describes a system for controlling a slave side camera with the emulators.

Section VIII: Describes a method for the automatic elimination of master-slave alignment offsets.

Section IX: Describes a motion tracking system that self-monitors the quality of its calibration.

Section X: Describes a system that adjusts the master/slave motion ratio based on the view of the operator.

Section XI: Describes a system for clutched roll.

I. Master/Slave Surgical System

FIG. 1 is an illustration of a conventional master/slave robotic surgical system 100, used to perform surgical operations. The system comprises a slave device 102 and a master device 104. The slave device comprises a surgical effector 106 that performs surgical procedures at a surgical site 108. The movements of the surgical effectors are a reproduction of movement representative of the surgical procedure performed by the operator 110 at the master device. The master/slave surgical system operates in one of three modes: active, alignment, or camera. Active mode engages during standard surgical procedures, alignment mode during alignment of the master and slave devices, and camera mode for the manipulation of the camera near the surgical site.

Master/slave surgical systems include one or more robotic surgical tools configured to be manipulated by encoded signals. The encoded signals will typically be electronic signals sent via wire or wirelessly from a remote location, where the operator is controlling the master device, to the location where the surgical effectors are being robotically manipulated by the slave device.

The master device includes one or more surgical tool emulators which correspond to at least some of the surgical effectors being controlled by the slave device at the surgical site. Oftentimes these emulators are mounted to and supported by the master device as a set of joysticks or similar.

In the embodiments presented hereafter, motion tracking technology removes the need for the joysticks used in traditional master/slave systems. The master device comprises a motion tracking system to track and interpret the motion of the emulators and computational system for translation of master device movements to slave device surgical effectors at the surgical site.

II. Motion Tracking System

FIG. 2 demonstrates a three-dimensional motion tracking system 200 including a motion tracking apparatus 202 and a computational system 204. The motion tracking apparatus is in the form of an open space surrounded by a system of detectors 206 mounted on supportive stanchions 208. The system of detectors is capable of tracking the position and motion of objects within a FWS 210. The system of detectors is coupled to the computational system such that encoded signals from the detectors can be received and interpreted by the computational system which may generate a set of motion instructions for the slave device.

The motion tracking apparatus may be constructed as a controlled environment with the system of detectors at predefined locations within the environment and the FWS being confined within the controlled environment. The controlled environment may be configured as a box with the one face removed, as a box with three adjacent faces and the other faces removed, as a box with two opposing faces and the other faces removed, a platform, or the like.

The system of detectors may include a set of video cameras mounted to stanchions surrounding the FWS. The cameras are electronically coupled to a computational system capable of simultaneously inputting multiple video sources, recognizing independent objects within the FWS, calculating orientation metrics of objects within the FWS, interpolating multiple two-dimensional sets of orientation metrics into three dimensions, calculating the relative orientation metrics between objects within the FWS, and translating the orientation metrics as a set of motion instructions for the surgical tool.

The orientation metrics are independently monitored for each object within the FWS (further elaborated below) and may include position, pitch, yaw, roll, speed, acceleration, distance, and similar. Alternatively, the system of detectors may include any method capable of determining the orientation metrics of objects within the FWS including infrared sensors, acoustic sensors, and similar.

The FWS represents the area that objects and their orientation metrics are able to be accurately measured by the motion tracking apparatus. The position, size, and shape of the FWS may be determined by the relative positions of the detectors making up the system of detectors. Additionally, the position, size, and shape of the FWS are limited by the computational system to prevent movement of the surgical tool outside a set of positional boundaries representing areas the surgical tool should not (e.g. vulnerable tissue) or cannot access (e.g. outside of slave motion constraints). Finally, the position size and shape of the FWS may be specifically constructed to represent the space being manipulated by the surgical system.

III. Operative Introduction to the Operative Modes of the Master/Slave Surgical System As briefly introduced above, the master/slave surgical system operates in one of three modes: active, alignment, or camera. Active mode for use during standard surgical procedures, alignment mode during alignment of the master and slave devices, and camera mode for the manipulation of the camera near the surgical site. FIGS. 3A-3E illustrates these operative modes of the master slave surgical system 300 and how changes in the orientation metrics of the emulators within the FWS translates to movement of the effectors or camera at the surgical site in the various operative modes.

FIG. 3A illustrates a two-dimensional projection of the FWS 302 and the objects within. The user's hands 304 and the emulators 306, hereafter in combination referred to as the emulators for clarity of description, within the FWS are monitored by the detector system configured to track their motion 308 (i.e., orientation metrics) as part of the master device in active mode.

Figure 3B:
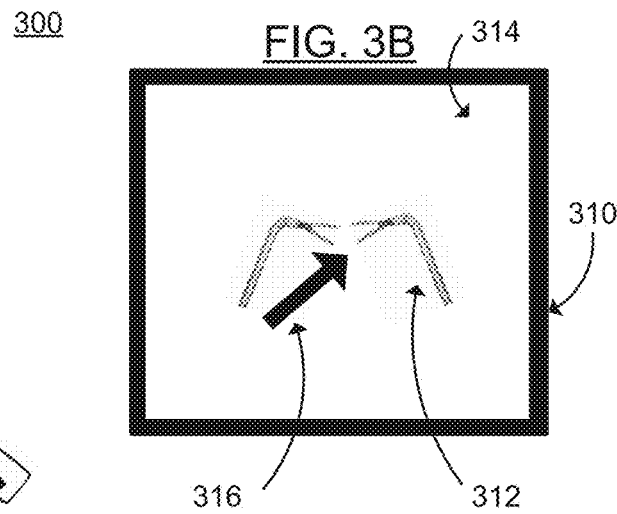
FIG. 3B illustrates an embodiment of slave device effector movement shown on a video display while the master/slave surgical system is in active mode.

FIG. 3B illustrates a video display 310 showing the slave surgical effectors 312 at the surgical site. When the master/slave surgical system is operating in active mode 314, changes in the orientation metrics of the emulators within the FWS are translated into motion of the surgical effectors 316 at the surgical site which is shown on the video display.

The video display component may be any number of devices capable of representing visual information such as a television screen, a computer screen, projected images on a surface, a personal media display device, a heads up display or the like. The visual display may be generated by a three-dimensional camera, a stereoscopically-arranged pair of cameras, or a three-dimensional representation of space created from a plurality of two-dimensional image sources, and similar. The corresponding visual display may be viewed in a method used to present three-dimensional video displays such as a stereoscopic device, goggles with augmented reality, a virtual reality system, a holographic display system and similar.

Figure 3C:
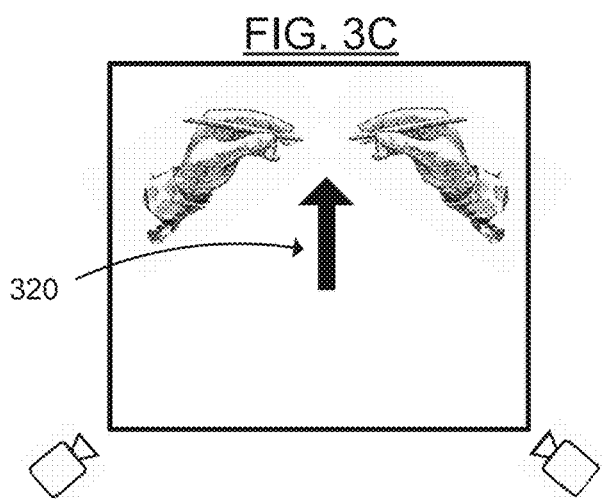
FIG. 3C illustrates an embodiment of master device movement within the free working space while the master/slave surgical system is in camera mode.

FIG. 3C illustrates a similar system as FIG. 3A for tracking the emulators within a FWS using a detector system configured to track their motion 320 as part of the master device in camera mode.

Figure 3D:
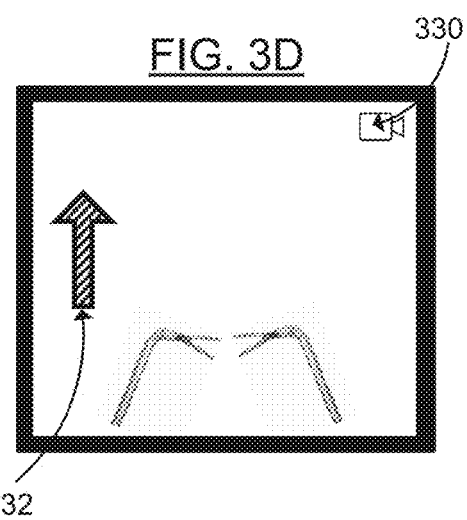
FIG. 3D illustrates an embodiment of slave device camera movement changing the field of view on video display while the master/slave surgical system is in camera mode.

FIG. 3D illustrates a video display showing the slave surgical effectors at the surgical site while the master/slave system is operating in camera mode 330. While in camera mode, changes in the orientation metrics of the emulators within the FWS are translated into motion of the camera at the surgical site. Motion of the camera at the surgical site moves the field of view 332 shown on the video display.

Figure 3E:
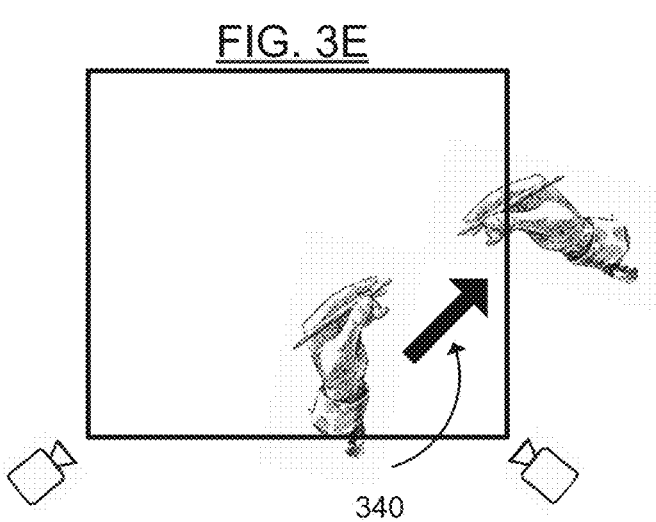
FIG. 3E illustrates an embodiment of master device movement within the free working space while the master/slave surgical system is in alignment mode.

FIG. 3E illustrates a similar system as FIG. 3A for tracking emulators within a FWS using a detector system configured to track their motion 340 as part of the master device in alignment mode.

Figure 3F:
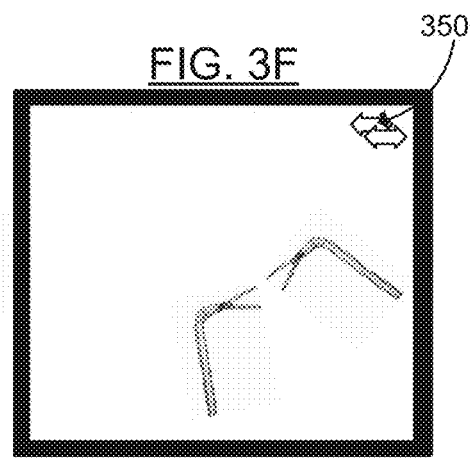
FIG. 3F illustrates an embodiment of slave device effector inactivity on a video display while the master/slave surgical system is in alignment mode.

FIG. 3F illustrates a video display showing the slave surgical effectors at the surgical site while the master/slave system is operating in alignment mode 350. While in alignment mode, motion of the effectors and the camera at the surgical site are terminated, i.e. changes in the orientation metrics of the emulators within the FWS are not translated into motion of the camera or the effectors at the surgical site.

During operation of the master/slave surgical system, it may be necessary for the operator to change between operative modes. These changes may be accomplished via a command to the master device. The command may include a keyboard input, a mouse button click, a vocal command or similar. Alternatively, the master system may be calibrated to automatically shift between operative modes in specific circumstances or situations that may be present at the slave device or the master device. Several of these systems are discussed below.

Note that FIGS. 3A, 3C, and 3E are representative of a video input received by the computational system from the detector system and do not necessarily illustrate a video display showing the emulators within the FWS, however some systems may include such a display.

IV. Haptic Response to Indicate Mater-Slave Alignment has been Achieved.

During complex surgical procedures involving a master/slave surgical system the master device translates the operator's actions in to actions performed by the slave device at the surgical site. To do this, the operator aligns the master and slave devices before the surgical procedure begins. During robotic surgeries the operator is inundated with the auditory and visual stimuli present in the operating room. Aligning the master and slave components without an auditory or visual cue may alleviate the stimulus saturation present in surgical situations and facilitate easier operation. As one way to do this, FIGS. 4B-4C and the discussion below illustrate a system for introducing haptic feedback to assist the operator in the alignment of a master/slave surgical system 400.

Figure 4A:
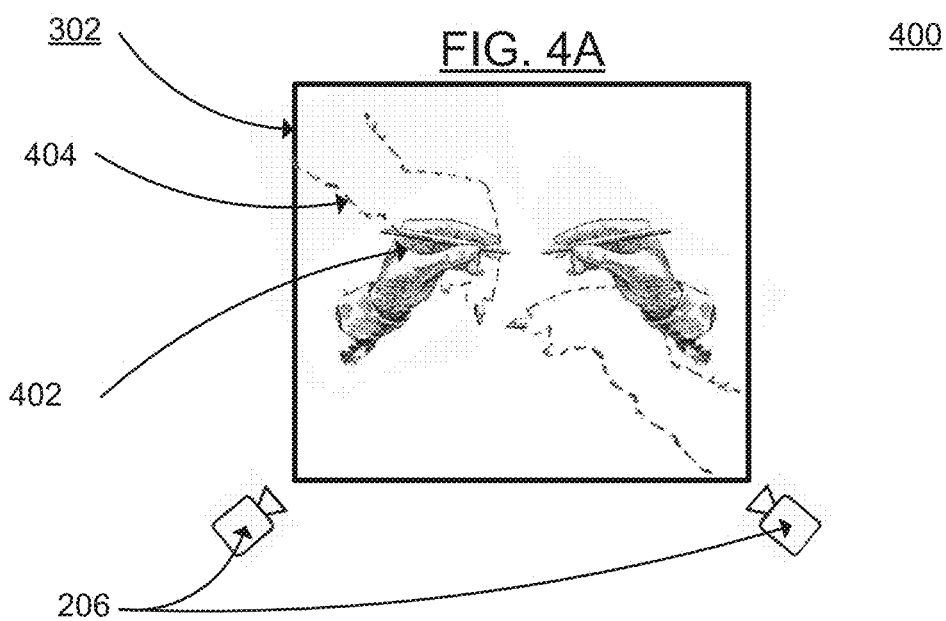
FIG. 4A illustrates representative effectors and emulators within a free working space, according to one embodiment.

Similarly to FIG. 3A, FIG. 4A illustrates a two-dimensional projection of the emulators within the FWS which are monitored by the detector system configured to track their motion as part of the master device. The computational system concurrently monitors orientation metrics of the slave surgical effectors at the surgical site and the orientation metrics of the emulators within the FWS. Additionally, the computational system creates and monitors a set of orientation metrics within the FWS representing the orientation metrics of the slave surgical effectors at the surgical site, hereafter the representative effectors. Note that the representative effectors exist only within the computational system and are only illustrated in the Figures for ease of understanding.

Hereafter, current orientation metrics of an object monitored by the computational system are referred to as a position, e.g. the position of the emulators 402, and the position of the representative effectors 404; changes in orientation metrics of an object monitored by the computational system are referred to as movement, e.g. move (or movement of) the surgical effectors; and differences in the orientation metrics between separate objects monitored by the computational system are referred to as a relative misalignment, e.g. the relative misalignment between the representative effectors and the emulators.

Ideally, during active mode operation, there is no relative misalignment between the representative effectors and the emulators. However, before or during surgical procedures a relative misalignment between the representative effectors and the emulators may be present or introduced over time due to various causes. When the relative misalignment between the representative effectors and the emulators is above a certain threshold quantitative or qualitative value, the system will enter alignment mode.

Figure 4B:
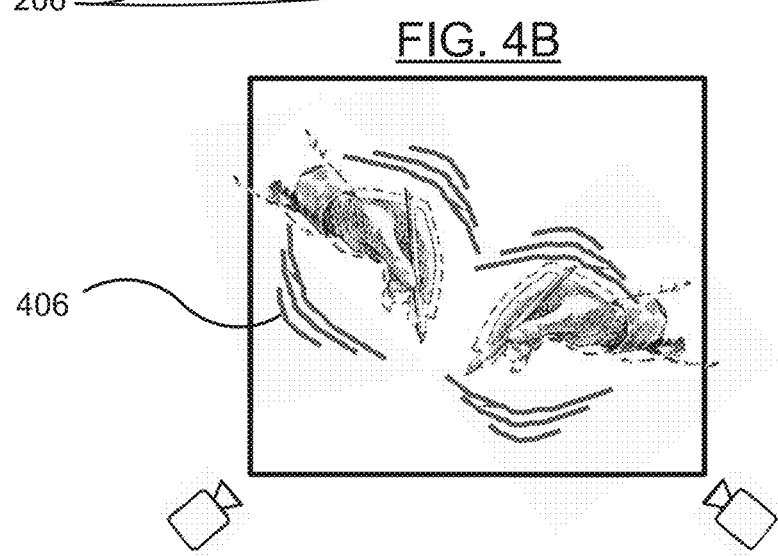
FIG. 4B illustrates a system for providing haptic feedback during alignment of a master/slave surgical system, according to one embodiment.

As illustrated in FIG. 4B, while the system is in alignment mode the user may move the position of the emulators towards the position of the representative effectors in the FWS. When the relative misalignment between the emulators and the representative effectors in the FWS is below a threshold defined in the computational system the emulator gives a haptic feedback response 406. The feedback response may be in the form of a pulse, vibration, click, temperature change, texture change, size change, or similar. Once the haptic feedback response has been given, the user may choose to leave alignment mode and enter active or camera mode.

Alternatively, rather than originating from the emulator, the haptic feedback response may originate from a component associated with the surgical tool system that is not the emulator, such as an armrest, a wrist strap, eyewear, supportive surfaces, gloves, or similar. Further, there may be different forms of haptic feedback that each represent different aspects of the surgical procedure, such as relative misalignment of the emulators and the surgical effectors, mishandling of the emulators, elapsing time, patient condition, and similar.

V. Handling Master Motion Outside Slave Motion Limits.

During a procedure utilizing a master/slave system to perform robotically assisted surgery, the slave device may have a limited range of motion due to the type of surgery, condition of the patient, nearby tissues types or various other limiting factors. When the slave device is operating in this type of environment, the user of the master device may move the emulators in the FWS to a position outside the range of motion of the surgical effectors and may create conditions that may result in a misalignment between the emulators and the effectors. The embodiments described hereafter allow for the alignment of the master/slave system after a relative misalignment between the representative effectors and the emulators near the limits of surgical effector movement 500.

A. Optimal Method for General Surgical Procedures.

FIG. 5A illustrates a two-dimensional projection of the position of the emulators and the position of the representative effectors within the FWS. The emulators are monitored by a detector system configured to track their motion as part of the master device. The position of the emulators, the position of the representative effectors, and the relative misalignment between the two are all monitored by the computational system. As discussed above, the surgical effectors may have a limited range of motion and operate in a limited working area (LWA) 510. The computational system monitors the boundaries of the LWA and creates and monitors a corresponding set of representative boundaries within the FWS 502, hereafter the representative LWA 502.

FIG. 5B illustrates a video display showing the surgical effectors at the surgical site during active mode operation. The surgical effectors operate within boundaries of the LWA 510 and motion outside of those boundaries is not allowed. The LWA is monitored by the computational system which also creates and monitors the representative LWA 502 within the FWS as shown in FIG. 5A. While there is no relative misalignment between the emulators and the representative effectors and the surgical effectors remain within the LWA the master/slave surgical system operates in active mode.

FIG. 5C illustrates an instance in which the position of the emulators moves 520 outside the boundaries of the representative LWA 502. The surgical effectors reach the boundaries of LWA at the surgical site (they are now at the limit of their range of motion) and cease movement causing the position of the representative effectors to persist at the boundaries of the representative LWA 522. This creates a relative misalignment between the position of the surgical effectors 530 and the position of the emulators 524. When the relative misalignment measured by the computational system moves above a threshold, the master/slave surgical system may automatically enter alignment mode.

FIG. 5D illustrates the video display in the instance where the position of the emulators moves outside the boundaries of the representative LWA 502. The position of the surgical effectors at the surgical site reach the limit to their range of motion and the boundaries of the LWA 530 causing the surgical effectors cease movement.

While in alignment mode, the user works to reestablish alignment of the master/slave surgical system. As shown in FIG. 5E, the user may move the position of the emulators 540 towards the position of the representative effectors in the FWS. The position of the representative effectors has persisted at the boundary of the representative LWA 542 because motion of the surgical effectors at the surgical site has been disallowed. When the position of the emulators matches the position of the representative effectors within the FWS and the relative misalignment between the two 544 drop below a threshold defined in the computational system, the master/slave surgical system may automatically reenter active mode.

In some cases when the master/slave surgical system reenters active mode, the position of the emulators and the position of the representative effectors are in close proximity to boundaries of the representative LWA. Small, subsequent motions of the emulators may quickly result in relative misalignments between the representative effectors and the emulators that result in automatically reentering alignment mode.

To prevent this, when the master/slave surgical system initially reenters active mode, the computational system may create a new adjusted representative LWA 546 which replaces the original representative LWA. The adjusted representative LWA still corresponds to the boundaries of the LWA at the surgical site; however, the boundaries of the adjusted representative LWA have been moved within the FWS by the computational system to allow more movement by the emulators before reaching the boundaries of the adjusted representative LWA and creating misalignment that would create a need to re-enter into alignment mode.

FIG. 5F illustrates the video display in the case where the position of the emulators and the position of the representative effectors match and there is no longer relative misalignment. The position of the surgical effectors remains at the boundaries of the LWA 550 as the motion of the effectors ceased when the master/slave surgical system automatically entered alignment mode. Now that the relative misalignment has been corrected the tool may reenter active mode and movement of the surgical effectors again reflects motion of the emulators in the FWS, assuming the emulator's motion remains within the adjusted representative LWA 546.

The realignment system outlined in the above discussion of FIGS. 5A-5F for a master/slave surgical system utilizing gesture tracking technology represents an exemplary embodiment. However, there are several other embodiments to handle potential relative misalignment between the emulators and the representative effectors when the surgical effectors are operating near the boundaries of the LWA.

B. Alternative Method Allowing Relative Misalignments Below a Tolerance.

During some surgical procedures, automatically entering alignment mode due to small relative misalignments when operating near the boundaries of the LWA may not be necessary. In this situation, the computational system may have a secondary spatial or temporal tolerances associated with the relative misalignment threshold that triggers entering alignment mode. The spatial tolerance allows slight movements above the relative misalignment threshold before entering alignment mode. The temporal tolerance allows movements with relative misalignment above the threshold for a small period of time before entering alignment mode. If the relative misalignment between the emulators and the representative effectors does not decrease below the threshold before the temporal or spatial tolerances are surpassed, the system will automatically enter alignment mode. If the relative misalignment decreases below the threshold before the tolerances are surpassed, the system will remain in active mode.

This would be represented on the video display as the surgical effectors temporarily ceasing movement at the edge of the LWA without entering alignment mode. The surgical effectors begin moving again if the relative misalignment is corrected. If the relative misalignment is not corrected, the effectors will remain motionless and the master/slave surgical tool enters alignment mode.

C. Alternative Method Allowing Relative Misalignments in Specific Areas.

Generally, the LWA (and the corresponding representative LWA) is a three-dimensional space with a set of boundaries in which the surgical effectors are able to move and operate. In many surgical procedures the boundaries of the LWA represent areas that should not be accessed by the surgical effectors (e.g. vulnerable tissues) and motion of the emulators that would cause movement of the effectors into these areas should trigger cessation of effector movement.

However, in some surgical procedures, specific boundaries of the LWA may represent areas that are non-critical. When the emulators move outside the boundary of the representative LWA in a non-critical area, automatically entering alignment mode may be detrimental to the overall surgical procedure. In this situation, the motion tracking system may instead translate the movement of the emulators outside the representative LWA into movement of the surgical effectors representing some projection of the movement onto the boundary of the LWA. This would be demonstrated on the video display as the surgical effectors sliding along the range of their motion limits without entering alignment mode.

As an alternative in a similar surgical procedure, when the emulators move outside the representative LWA in a non-critical area the surgical effectors cease movement at the boundaries of the LWA at the surgical site. The emulators may reenter the boundaries of the representative LWA at a different non-critical position from where they exited the representative LWA. When this occurs, the surgical effectors may automatically move to a position within the boundaries of the LWA computed from the new position of the emulators in the representative LWA. The position of the representative effectors is automatically set to the current position of the emulators after the movement of the surgical effectors. This would be demonstrated on the video display as the surgical effectors ceasing movement at one point at the boundary of the LWA and subsequently moving to a new position within the LWA after some time without entering alignment mode.

Any process that functions to realign the master/slave surgical system, for example those described in this subsection, may allow for the computation and creation of an adjusted representative LWA similar to the system illustrated in FIG. 5E.

VI. Detection of User's Grip on the Master Controllers.

Figure 6:
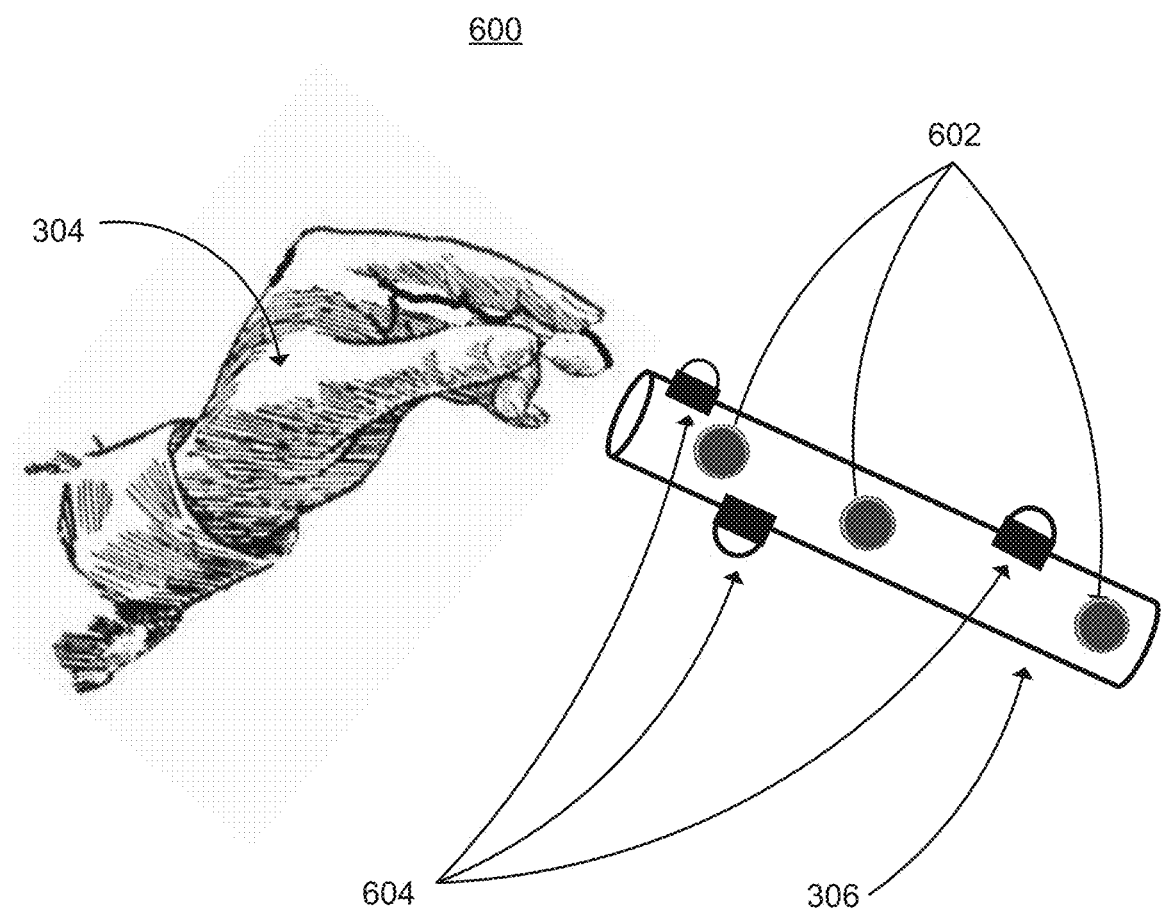
FIG. 6 illustrates an emulator designed for grip detection, according to one embodiment.

The master/slave surgical system relies on the operator to control emulators on the master device that represent and control surgical effectors on the slave device FIG. 6 shows a surgical emulator designed to identify unintended emulator movements 600. The surgical emulator can be held in the operator's hand and is designed to be a representation of the surgical effector at the surgical site. The emulator has at least one or more touch activated sensors 602 and/or light emitting/reflecting surfaces 604. The emulator may be wirelessly coupled or connected via umbilical to the master device. The master device and the emulator may both produce and receive signals for controlling the state of any sensor, light emitting surface, or light reflective surface that may make up the emulator.

The touch activated sensors may be any component or set of components used to detect the grip of the operator, such as capacitive pads, force-sensitive resistors, switches, pressure-activated switches, infrared detector and emitter pairs, or similar. The light emitting or reflective surfaces may be any component or set of components that would be occluded by the normal grip of the operator such as, light emitting diodes, fluorescent materials, lasers, reflective tape, metallic surfaces, or similar.

In an exemplary embodiment, the master device is wirelessly coupled to the emulator which consisting of capacitive pads in an orientation such that the operator's normal grip on the emulator will create and transmit an encoded signal to the master device indicating that the emulator is being held in the operator's hand in an operative manner. In the event that the operator's grip becomes abnormal and changes the interaction with the capacitive pads, the emulator will create and transmit an encoded signal to the master device indicating the emulator is not being held in an operative manner. When this signal is received the master device may disengage active mode, cease the movement of the surgical effectors at the surgical site, and enter alignment mode until normal handling of the emulator is restored.

In another design, the emulator utilizes light emitting diodes in an orientation such that the operator's normal grip on the emulator occludes the light from being emitted. The motion tracking system is further configured to detect the appearance of the light emitted by the light emitting diodes when the operator's normal grip is compromised. When the light is detected, the master device may disengage active mode, cease the movement of the surgical effectors at the surgical site, and enter alignment mode until normal handling of the emulator is restored.

Alternatively, the emulator may not be specifically designed to signify changes in the users grip. The detector system and the computational system may be further configured to recognize the operator's normal and abnormal grip on the emulator via object, gesture, or motion recognition algorithms.

VII. Camera Control of a Master/Slave System that Prevents Rotational Misalignment During the operation of a master/slave surgical system in active mode, the orientation of the medical devices (e.g., surgical effectors, tools, devices, or instruments) may make viewing specific areas difficult when the medical devices are in the desired line of sight of the camera monitoring a specific area at the target site (e.g., a surgical site). The ability to manipulate the position of camera at the surgical site and the corresponding field of view on the video display using the emulators is advantageous, providing a more streamlined surgical operation.

FIGS. 7A-7F depict a camera control system for a master/slave surgical system 700. In one aspect of the disclosure, the system 700 comprises emulator(s) (e.g., the emulators 402) configured to be held and operated in a FWS (e.g., the FWS 302), the emulator(s) representing medical device(s) (e.g. surgical effectors) at the target site. The system 700 may comprise one or more detectors (e.g., the detectors 206 or imaging device(s)) may be configured to track the emulator(s) within the FWS. The system 700 may comprise: at least one computer-readable memory having stored thereon executable instructions; and at least one processor in communication with the at least one computer-readable memory and configured to execute the instructions to cause the system 700 to perform steps as described below. In camera mode, the motion tracking system interprets translational movement of the emulators to be translational movement of the camera position. Consequently, in camera mode translational movement of the emulator does not correspond/result in translational movement of the surgical effectors. However, in camera mode rotational motion of the emulators does result in rotational motion of the surgical effectors. Consequently, in camera mode rotational movement of the emulator does not result in rotational motion of the camera.

In this example, FIG. 7A illustrates a two-dimensional projection of the position of the emulators and the position of the representative effectors within the FWS. While in active mode, the translational movement 702 of the emulators is monitored by a detector system configured to track the emulator motion as part of the master device.

FIG. 7B illustrates a video display 310 showing the surgical effectors at the surgical site during active mode operation. The movement of the emulators is translated into motion of the surgical effectors at the surgical site 710. While in active mode, translational movement 712 and rotational movement 714 of the camera are not allowed.

To continue, as illustrated in FIG. 7C, the operator may engage camera mode to change the position of the camera and the corresponding field of view on the video display. In this mode, translational movement of the emulators 720 within the FWS is monitored by the detector system.

FIG. 7D illustrates that in camera mode, translational movement of the camera is allowed and a translational movement of the emulators does not generate movement for the surgical effectors 730, but instead generates translational movement of the camera 732 altering the field of view on the video display.

Finally, as illustrated in FIG. 7E, rotational movement of the emulators 740 within the FWS is monitored by the detector system while still in camera mode.

FIG. 7E illustrates that in camera mode a rotational movement of the emulators generates movement for the surgical effectors limited to rotational motions 750. Rotational movement of the camera is disallowed in camera mode.

Note that FIGS. 7A, 7C, and 7E are representative of a video input received by the computational system from the detector system and do not illustrate a video display showing the emulators within the FWS.

In related aspects, the at least one processor may be configured to execute the instructions to cause the system to: receive a signal from at least one detector indicative of a translational movement of the emulator within the FWS; and generate instructions, based on the translational movement of the emulator, to move an imaging device within a plane defined by pitch and yaw axes of the imaging device. In one embodiment, translational movement of the emulator does not result in a translational movement of the medical device.

The at least one processor may be further configured to execute the instructions to cause the system to receive a signal from the at least one detector indicative of a rotational movement of the emulator within the FWS; and generate instructions, based on the rotational movement of the emulator, to rotate the medical device along a roll axis of the medical device. In one embodiment, rotational movement of the emulator does not result in a rotational movement of the imaging device.

VIII. Automatic Ratcheted Elimination of Master Slave Alignment Offsets

During operation of the master/slave surgical system in active mode, the relative alignment offset (i.e., misalignment) between the emulators and the representative medical devices (e.g., surgical effectors, tools, devices, or instruments) in the FWS may increase but remain below the tolerance that would trigger a transition from active mode to alignment mode. The slight misalignment is allowed to reduce the total time it takes for the user to achieve adequate alignment.

However, it is desirable to reduce misalignment without necessarily requiring activation of alignment mode or any other additional effort from the user.

In one aspect of the disclosure, a system may comprise: an emulator configured to be held and operated in a FWS, the emulator representing a medical device at a target site; at least one detector configured to track the emulator within the FWS; at least one computer-readable memory having stored thereon executable instructions; and at least one processor in communication with the at least one computer-readable memory and configured to execute the instructions to cause the system to perform the method as described below.

FIGS. 8A-8F depict a representation of a method to automatically reduce the relative misalignment between the emulators and the representative effectors within the FWS 800 using what is herein referred to as "ratcheting" technique, which is described in the following paragraphs.

Figure 8A:
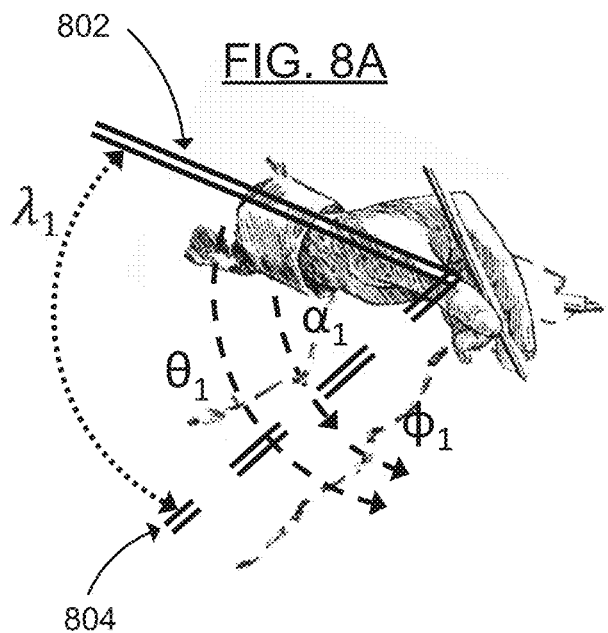
FIG. 8A is an illustration of the emulators and the representative effectors during the first iteration of the ratcheting process, according to one embodiment.

FIG. 8A depicts a linear representation of the position of the emulators 802 and a linear representation of the position of the representative effectors 804. Additionally, FIG. 8B depicts a linear representation of the position of the surgical effectors 810.

In this example, $\lambda_n$ is the relative misalignment between the position of the emulators and the position of the representative surgical effectors. $\alpha_n$ is a movement of the emulators the generates a corresponding movement of the effectors $\omega_n$, where the two will generally differ from each other with respect to position orientation metrics but not rotation orientation metrics. $\varphi_n$ is an additional movement of the emulators to create a total movement $\theta_n$ that reduces the relative misalignment $\lambda_n$.

Figure 8B:
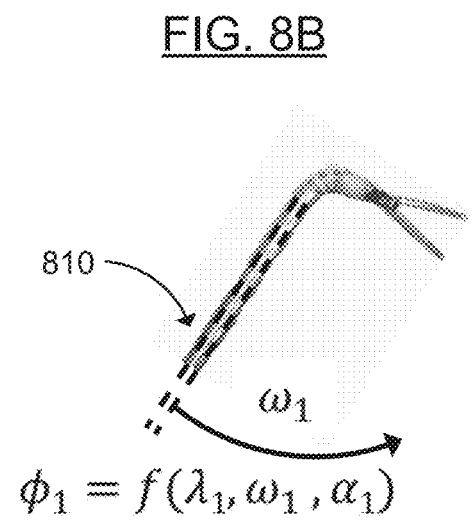
FIG. 8B is an illustration of the effectors during the first iteration of the ratcheting process, according to one embodiment.

To elaborate using FIGS. 8A and 8B, the surgical system is operating in active mode with a relative misalignment $\lambda_1$ between the emulators and the representative effectors. The operator moves the emulators by $\alpha_1$ to create a corresponding movement of the slave surgical effectors $\omega_1$ at the target site, such as, for example, the surgical site. Traditionally, an operator movement of $\alpha_1$ creates a direct translation of motion to the surgical effectors $\omega_1$. In this example, the computational system computes an additional (or lesser) amount of movement $\varphi_1$ as a function of $\lambda_1, \omega_1, \alpha_1$ that when added to (or subtracted from) $\alpha_1$ represents the total actual movement of the emulators $\theta_1$ (i.e., $\theta_1 = \alpha_1 + \varphi_1 = \alpha_1 + f(\lambda_1, \omega_1, \alpha_1)$) that creates the movement $\omega_1$. The movement of the emulators by $\theta_1$ yields a lesser relative misalignment between the emulators and the representative effectors.

Figure 8C:
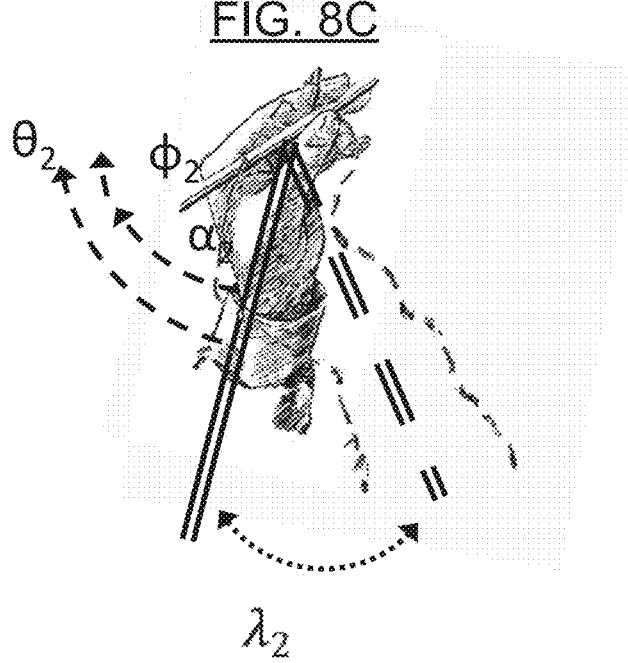
FIG. 8C is an illustration of the emulators and the representative effectors during the second iteration of the ratcheting process, according to one embodiment.
Figure 8D:
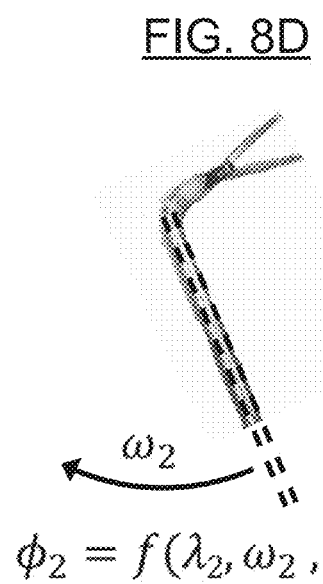
FIG. 8D is an illustration of the effectors during the second iteration of the ratcheting process, according to one embodiment.
Figure 8E:
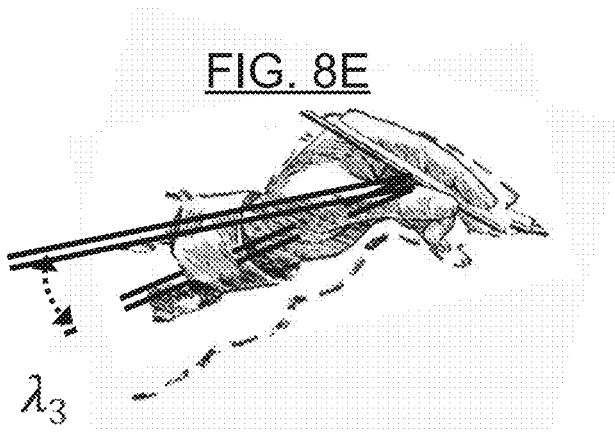
FIG. 8E is an illustration of the emulators and the representative effectors during the third iteration of the ratcheting process, according to one embodiment.
Figure 8F:
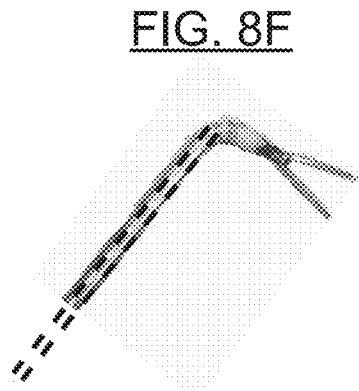
FIG. 8F is an illustration of the effectors during the third iteration of the ratcheting process, according to one embodiment.

This example continues using FIGS. 8C and 8D wherein the same process occurs with $\lambda_2$ being the lesser relative misalignment between the emulators and the representative effectors resulting from the total movement $\theta_1$. The computational system computes an additional (or lesser) amount of movement $\varphi_2$ as a function of $\lambda_2, \omega_2, \alpha_2$ that when added to (or subtracted from) $\alpha_2$ represents the total actual movement of the emulators $\theta_1$. The movement of the emulators by $\theta_2$ yields an even smaller in magnitude relative misalignment between the emulators and the representative effectors. This process continually iterates as in FIGS. 8E and 8F until the relative misalignment $\lambda_n$ is neutralized.

It is possible for the computational system to calculate a specific additional movement $\varphi'_n$ that would neutralize the relative misalignment in a single iteration. While efficient, the single iteration may create a movement by the user that is unnatural (e.g. extreme over motions to compensate for smaller misalignments) and detrimental to the overall medical or surgical procedure. The total amount of movement $\theta'_n$ to neutralize the relative misalignment is built in a series of smaller additive movements over time, i.e. $\theta'_n = \Sigma_i^j \varphi_i$ where j is the number of iterations required to neutralize the relative misalignment. This iterative process can be described as 'ratcheting' down the misalignment, and the larger the number of iterations j the smoother the ratcheting process appears to the operator.

In related aspects, the at least processor may be configured to execute the instructions to cause the system to: determine an alignment offset between a location of the emulator and a location of the medical device; during a medical procedure, determine a first movement amount based on a signal from the at least one detector indicative of a first movement of the emulator within the FWS; adjust the first movement amount by a first adjustment value; and generate instructions to move the medical device based on the adjusted first movement amount, wherein movement of the medical device by the adjusted first movement amount reduces the alignment offset between the location of the emulator and the location of the medical device.

The at least one processor may be further configured to execute the instructions to cause the system to repeat the steps described above to further reduce the alignment offset. For example, the at least one processor may be further configured to execute the instructions to cause the system to: during the medical procedure, determine a second movement amount based on a signal from the at least one detector indicative of a second movement of the emulator within the FWS; adjust the second movement amount by a second adjustment value; and generate instructions to move the medical device based on the adjusted second movement amount, wherein movement of the medical device by the adjusted second movement amount reduces the alignment offset between the location of the emulator and the location of the medical device. In one embodiment, the movement of the medical device by the adjusted first and second movement amounts may eliminate the alignment offset between the location of the emulator and the location of the medical device. In another embodiment, the alignment offset between the location of the emulator and the location of the medical device may be eliminated after more than two adjustments or movements of the medical device.

IX. Tracking System that Self-Monitors the Quality of the Calibration.

The master/slave surgical system controlled via an optical motion tracking system requires calibration with one or more known objects in a known geometry before it can provide accurate tracking data. The calibration can be affected by many factors, such as lighting and temperature, and may change or degrade over time. It is desirable to maintain optimal calibration with minimal intervention from the user to create accurate translations of motion from the master device to the slave device in an efficient manner.

Figure 9:
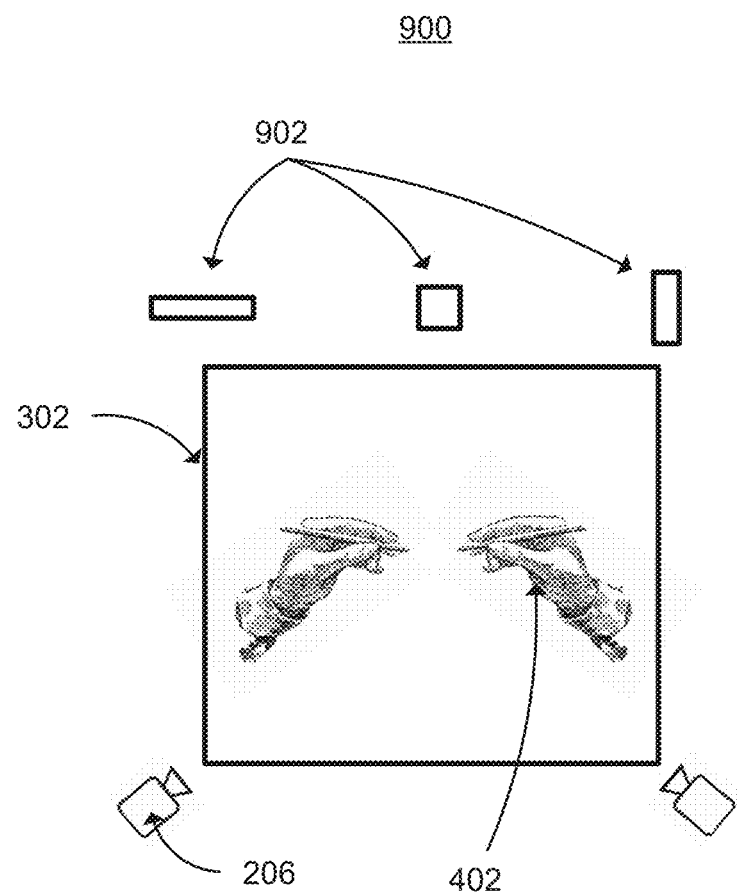
FIG. 9 illustrates a motion tracking system that self-monitors calibration, according to one embodiment.

FIG. 9 represents a motion tracking system that self-monitors the quality of the calibration 900. The position of the emulators within the FWS are monitored by the detector system configured to track their motion, depicted by a two-dimensional projection of the FWS and the objects within. The configuration of the detector system utilizes one or more known objects in a known orientation 902 in the field of view of the detector system.

Alternatively, the known objects may be a set of light sources or reflective surfaces that can be monitored by the detector system. The light sources may be light emitting diodes, infrared emitters, lasers, or similar. The reflective surfaces may be reflective tapes, metals, or similar. The known objects may also be a set of objects or surfaces.

The operator calibrates the motion tracking system with an orientation baseline using the known objects while the tool is in alignment mode. Once the operator engages active mode, the computational system actively compares the position of objects within the FWS to the orientation baseline created during calibration.

In the case where the relative misalignment between the measured position of the objects within the FWS and the orientation baseline is above a tolerance threshold the tool may indicate to the user that calibration has been compromised. Alternatively, when the misalignment between the measured position of the objects within the FWS and the orientation baseline is above a tolerance threshold the tool automatically recalibrates the orientation baseline using the position of the known objects.

X. View Based Automatic Adjustment of Master/Slave Ratio.

The surgical system has a translation ratio that represents the proportion of the magnitude of motion (change in orientation metric) that is translated from the emulators to the effectors. Depending on this ratio, an operator may have to move the emulators a greater or lesser distance to cause a certain amount of motion in the effectors.

If a surgical system has only a fixed translation ratio, or a translation ratio that is not easily changeable during surgical procedures, it is difficult for the operator to rapidly change or move between magnifications or fields of view used on the video display.

To address this, the master/slave surgical system is capable of motion scaling. For example, surgical effectors of the slave device may require much less movement than the operator's hands use in moving the emulators, allowing the operator to make comparatively larger motions to cause comparatively smaller/finer actions of the surgical effectors.

FIG. 10 represents a system that allow a high level of surgical control at various video display magnifications without requiring the surgeon to issue separate commands to adjust the translation ratio between the master device and slave device 1000.

Figure 10A:
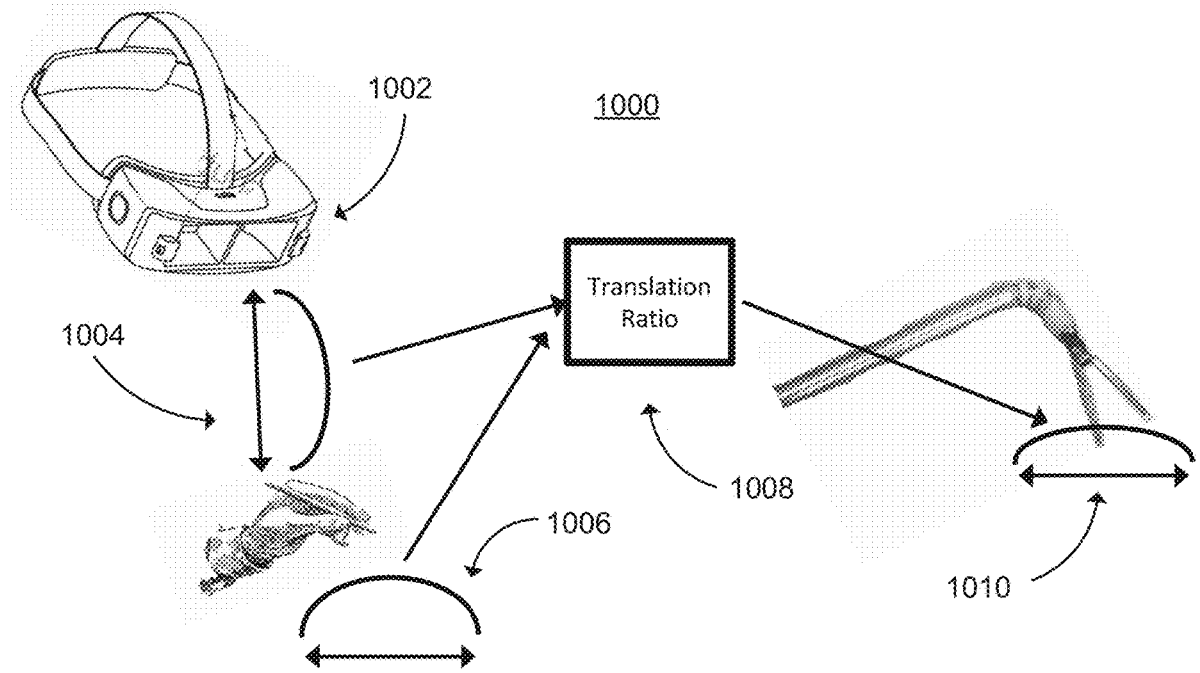
FIG. 10A illustrates a wearable surgical viewing system that translates a large magnification distance to large surgical effector movements, according to one embodiment.

As illustrated in FIG. 10A, the operator of the master device uses a video display comprising a wearable set of stereoscopic goggles 1002 that display an image of the surgical effectors at the surgical site. The goggles consist of a system that monitors and measures the distance between the goggle eyepieces and the emulators, hereafter the magnification distance 1004. The movement of the emulators 1006 is converted by the translation ratio 1008 into a movement of the surgical effectors 1010 based on the magnification distance. Thus, a change in a magnification distance, for example by the operator moving the googles closer to or further from the emulators, creates a corresponding change in the magnification distance, and therefore in the translation ratio.

Figure 10B:
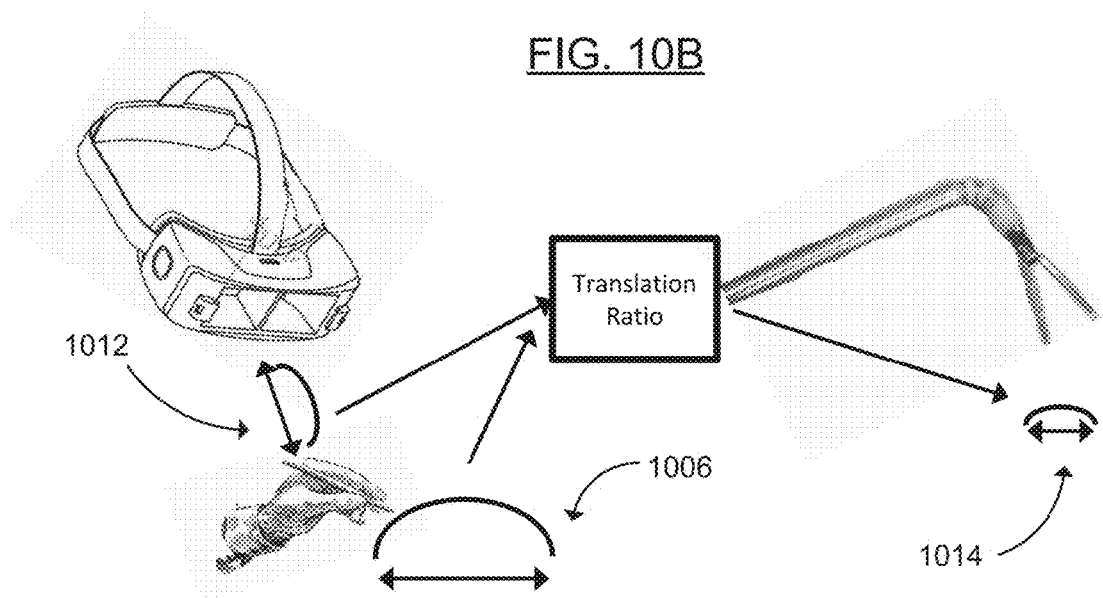
FIG. 10B illustrates a wearable surgical viewing system that translates a small magnification distance to small surgical effector movements, according to one embodiment.

A specific example of this is demonstrated in FIG. 10B. At a smaller magnification distance 1012 the translation ratio creates a smaller movement 1014 in the surgical effectors for a similar movement of the emulators. Similarly, though not shown, at a larger magnification distance the translation ratio creates a larger movement of the surgical effectors for a similar movement of the emulators.

The system that monitors and measures the magnification distance may comprise any components or set of components that would allow for the measurement of the magnification distance such as stereoscopic cameras mounted on the goggles, light sources and detectors mounted on the goggles and emulators, a camera mounted on the goggles and calibration markers on the emulator, or similar.

Alternatively, the magnification distance may be monitored by the same motion tracking system that monitors the position of the emulators, or by a motion tracking system configured to track the position of the operator's head or eyes relative to the emulators.

FIG. 11 represents another system which enables a high level of surgical control at various video display magnifications without forcing the surgeon to issue separate commands to adjust the translation ratio between the master device and slave device 1100.

Figure 11A:
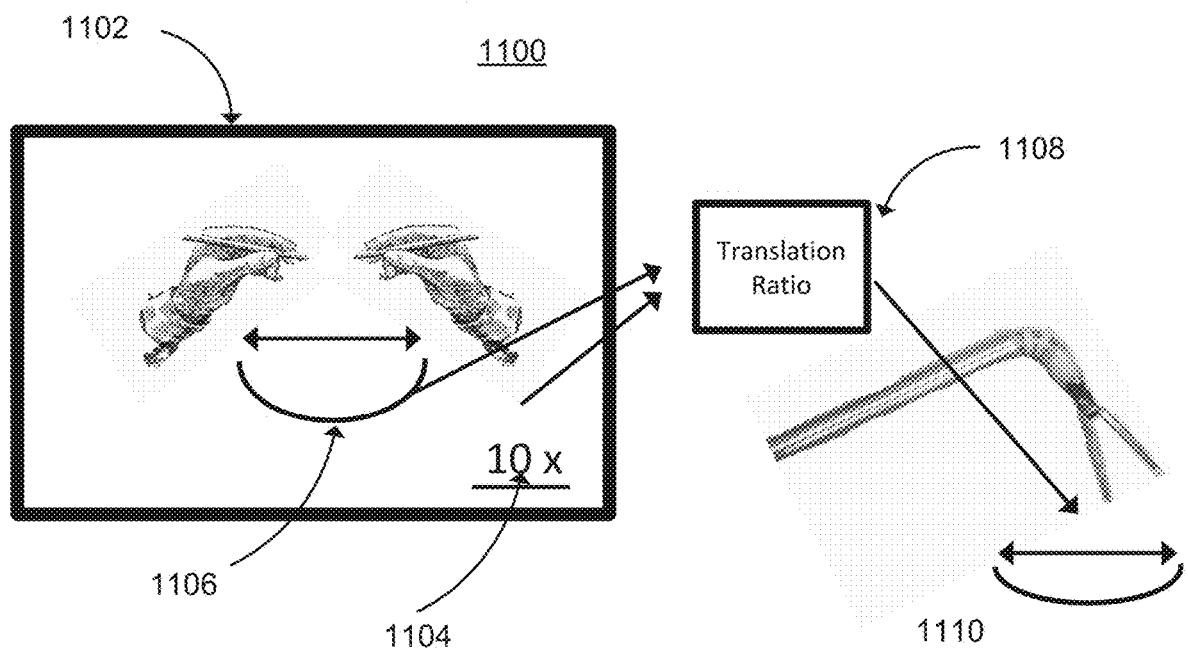
FIG. 11A illustrates a surgical viewing system with a changeable magnification setting that translates small magnifications to large surgical effector movements, according to one embodiment.

As illustrated in FIG. 11A, the operator of the master device uses a video display 1102 with a scalable magnification setting that displays the surgical effectors at the surgical site. At any point in time, the video display has a specific magnification setting 1104. A movement change of the emulators 1106 is converted by the translation ratio 1108 into movement of the surgical effectors 1110 based on the specific magnification setting.

Figure 11B:
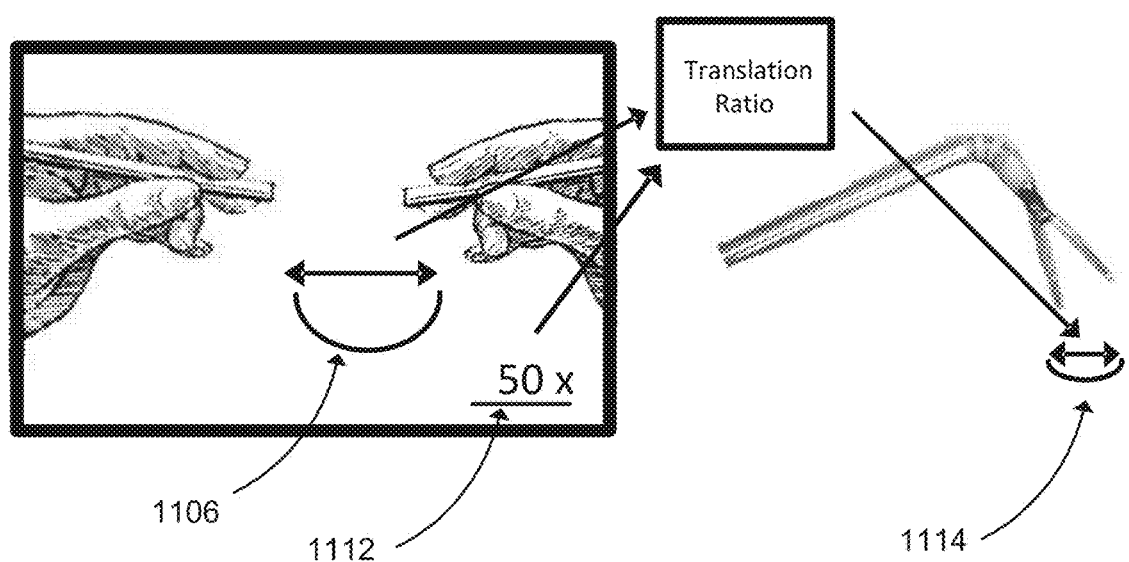
FIG. 11B illustrates a surgical viewing system with a changeable magnification setting that translates large magnifications to small surgical effector movements, according to one embodiment.

A specific example of this is demonstrated in FIG. 11B. At a larger magnification distance 1112 the translation ratio creates a smaller movement 1114 in the surgical effectors for a similar movement of the emulators. Similarly, though not shown, at a larger magnification distance the translation ratio creates a larger movement of the surgical effectors for a similar movement of the emulators.

XI. Clutched Roll

In one aspect of the present disclosure, there is provided a system wherein an operator (e.g., a physician or surgeon) controls an emulator that represents and controls a medical device (e.g., surgical effectors, tools, devices, or instruments). The system may be configured to control an instrument with extended roll capability, such as, for example, a medical device with an end-effector controlling or otherwise manipulating a curved needle.

The ability to control the medical device may be limited by the roll capability of an operator's wrist. For example, the operator may not be able to rotate his/her wrist beyond certain angles—for example, about 66.1° for pronation (i.e., rotation of the wrist such that the palm is facing downward or backward/posteriorly) or about 75° for supination (i.e., rotation of the wrist such that the palm is facing upward or forward/anteriorly). Thus, it may be desirable for the system to enable the operator to employ the extended roll capability of the medical device (e.g., extending the roll capability beyond that of the operator's wrist) and not be limited or hampered by the anatomical limitation of the operator (e.g., anatomical limitation of the operator's wrist). This can help the operator conduct tasks requiring extensive instrument roll, such as, for example, during suturing.

One aspect of the disclosure provides the operator with the ability to perform clutched roll of the medical device, allowing the operator to activate a clutch (e.g., a clutch foot pedal, button, or other input to activate the decoupling of the absolute roll angle of the medical device from that of the emulator) and thereby roll the medical device farther than his/her wrist could go. This clutched roll feature allows the operator to use a ratcheting turning motion to roll the instrument in one motion, pause the roll, and then continue rolling the instrument in a subsequent motion, while, in some cases, maintaining wrist yaw-pitch.

The clutched roll feature of the system facilitates decoupling an absolute roll angle of the medical device from an absolute roll angle of the emulator. The clutched roll of the medical device allows for decoupling the roll axis from the other axes of the medical device (i.e., the yaw axis or the pitch axis). In other words, rotational movements with respect to the roll axis of the emulator are not translated into rotational movements with respect to the roll axis of the medical device, whereas the rotational movements of the emulator with respect to the other axes are translated to the medical device.

FIGS. 12A-12F illustrate a system 1200 configured to perform a clutched roll. The system 1200 may comprise an emulator 1206 configured to be held and operated in a FWS (e.g., the FWS 302), the emulator representing a medical device 1214 at a target site; one or more detectors (e.g., detectors 206) configured to track the emulator 1206 within the FWS 302; one or more detectors configured to track the medical device 1214; at least one computer-readable memory having stored thereon executable instructions; and at least one processor in communication with the at least one computer-readable memory and configured to execute the instructions to cause the system to perform a clutched roll as described below.

FIG. 12A illustrates a two-dimensional projection of the position of the emulator 1206 and the position of the representative medical device 1214 within the FWS 302. The movement of the emulator 1206 (e.g., clockwise rotation by 90 degrees) is monitored by a detector system configured to track the motion of the emulator.

FIG. 12B illustrates a video display 310 showing the medical device at the target site during the non-clutched mode operation. During the non-clutched mode, the rotational movement 1208 of the emulator 1206 (e.g., clockwise rotation by 90 degrees) in all axes is translated into a rotational motion 1216 of the medical device 1214 at the target site (e.g., clockwise rotation by 90 degrees). In one aspect, the system 1200 may rotate the medical device 1214 based on the rotational movement of the emulator 1206 by, for example, conducting a spherical linear interpolation (slerp) of the current medical device quaternion towards the emulator quaternion. During the non-clutched mode, the operator may rotate the emulator with his/her wrist with respect to its roll axis as far as the anatomical structure of the wrist allows.

As illustrated in FIG. 12C, when the operator reaches the limit of how far he/she can rotate his/her wrist, the operator may activate a clutched roll mode of the system to decouple an absolute roll angle of the medical device 1214 from an absolute roll angle of the emulator 1206. As shown in FIG. 12D, in the clutched roll mode (as signified by a mark or icon 1230 on the video display 310), a rotational movement 1210 of the emulator 1206 (e.g., counterclockwise rotation by 90 degrees) within the FWS 302 with respect to its roll axis is not translated into a rotational movement 1218 of the medical device 1214 with respect to its roll axis. As a result, during the clutched roll mode, the operator may rotate his/her wrist to its original position with respect to its roll axis without moving the medical device 1214.

In one aspect of the disclosure, steps to conduct the clutched roll (as may be performed by the system 1200) are described below as follows. First, a cross product and a dot product of the z-vector of the emulator 1206 (e.g., a unit vector along the roll axis of the master device) and the z-vector of the medical device 1214 (e.g., a unit vector along the roll axis of the slave device) are computed. Then, the instantaneous rotation matrix is calculated using the following matrix formula:

$$R = \begin{bmatrix} \frac{cp[0] \cdot cp[0]}{wa} + ca & \frac{cp[0] \cdot cp[1]}{wa} - cp[2] & \frac{cp[0] \cdot cp[2]}{wa} + cp[1] \\ \frac{cp[1] \cdot cp[0]}{wa} + cp[2] & \frac{cp[1] \cdot cp[1]}{wa} + ca & \frac{cp[1] \cdot cp[2]}{wa} - cp[0] \\ \frac{cp[2] \cdot cp[0]}{wa} - cp[1] & \frac{cp[2] \cdot cp[1]}{wa} + cp[0] & \frac{cp[2] \cdot cp[2]}{wa} + ca \end{bmatrix}$$

wherein

R=instantaneous rotation matrix cp=a cross product vector of the z-vector of the emulator 1206 and the z-vector of the medical device 1214;

ca=a scalar of a cross product of the z-vector of the emulator 1206 and the z-vector of the medical device 1214; and wa=a dot product of the z-vector of the emulator 1206 and the z-vector of the medical device 1214.

The instantaneous rotation matrix R allows the alignment of the roll axis of the emulator 1206 and the roll axis of the medical device 1214 without consideration of the other axes (i.e., pitch and yaw axes) of the emulator 1206 or the medical device 1214. Then, the target orientation of the medical device 1214 is calculated from the current orientation of the slave device and the instantaneous rotation matrix as follows:

$v_f = R \times v_i$ wherein $v_i$=current orientation of the medical device 1214;

$v_f$=target orientation of the medical device 1214; and

R=instantaneous rotation matrix.

Then, the medical device 1214 is rotated based on the target orientation calculated above. The rotation of the medical device 1214 may be conducted by a variety of techniques including, but not limited to slerp or linear interpolation (lerp).

Finally, as illustrated in FIG. 12E, the operator can turn off the clutched roll mode and repeat rotating the emulator 1206. As shown in FIG. 12F, during the non-clutched mode, the rotational movement 1212 of the emulator 1206 (e.g., clockwise rotation by 90 degrees) in all axes is translated into a rotational motion 1220 of the medical device 1214 at the target site (e.g., clockwise rotation by 90 degrees). The operator may repeat the first step and the second step until the desired rotation is achieved.

Note that FIGS. 12A, 12C, and 12E are representative of a video input received by the computational system from the detector (e.g., detectors 206) and do not illustrate a video display showing the emulators within the FWS. In actual use of one embodiment, the operator's hand would be holding the emulator 1206. However, for purposes of showing the orientation of the emulator 1206 and the operator's hand in the FWS, the operator's hand is shown next to the emulator 1206 rather than over or covering the emulator 1206.

In one aspect of the disclosure, the surgical system may be monitored and/or controlled via a motion tracking system. In other words, one or more locations or motions of the medical device and/or the emulator may be tracked by the motion tracking system. The motion tracking system may be optical or electromagnetism (EM)-based. In another aspect of the disclosure, the clutched roll feature may be used in a system that does not utilize the motion tracking system. In one aspect of the disclosure, features disclosed in other sections may be used in a system that does not utilize motion tracking. In one aspect of the disclosure, the emulator may be a mechanical emulator, and the detectors may be configured to track the mechanical movement of the mechanical emulator and/or the operation of the mechanical emulator by the operator.

In related aspects, the system may comprise an emulator representing a medical device at a target site. The system may comprise a first set of one or more detectors configured to track the emulator. The system may comprise a second set of one or more detectors configured to track the medical device at the target site. The system may comprise at least one computer-readable memory having stored thereon executable instructions; and at least one processor in communication with the at least one computer-readable memory and configured to execute the instructions to cause the system to: receive, from the first set of one or more detectors, first data indicative of at least an orientation of the emulator, the first data comprising roll data, pitch data, and yaw data of the emulator; generate, based on a clutched user input, instructions to move the medical device based on the first data discounting the roll data of the emulator; and cause the medical device to move based on the instructions. In one embodiment, the emulator may be configured to be held and operated in a FWS; and the first set of one or more detectors may be configured to track motion of the emulator in the FWS. In one embodiment, the emulator may comprise a mechanical emulator; and the first set of one or more detectors may be configured to track mechanical movement of the emulator.

In one embodiment, the discounting of the roll data of the emulator may be based on decoupling a roll axis of the emulator from yaw and pitch axes of the emulator. In one embodiment, the discounting of the roll data of the emulator may be based on decoupling an absolute roll angle of the medical device from an absolute roll angle of the emulator. In one aspect, the movement of the medical device based on the instructions may facilitate adjustment of a roll axis of the emulator with respect to a roll axis of the medical device.

In one embodiment, the at least one processor may be configured to execute the instructions to cause the system to receive, from the second set of one or more detectors, second data indicative of an orientation of the medical device at the target site, the second data comprising roll data, pitch data, and yaw data of the medical device; and the alignment of the respective roll axes of the emulator and the medical device is based on the pitch and yaw data of the emulator and the pitch and yaw data of the medical device.

In one embodiment, the at least one processor may be configured to execute the instructions to cause the system to: receive, from the first set of one or more detectors, third data indicative of a translational movement of the emulator; receive, from the second set of one or more detectors, fourth data indicative of a position of the medical device at the target site; and generate instructions to move the medical device based on the third and fourth data.

Figure 13A:
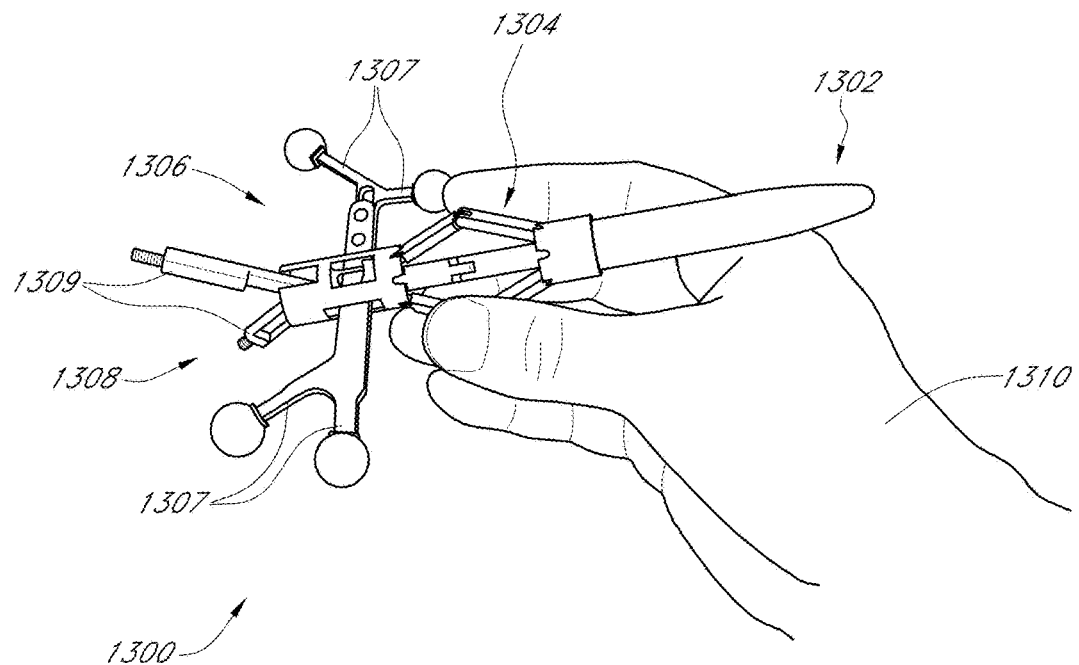
FIGS. 13A-13B illustrate an emulator, according to another embodiment.
Figure 13B:
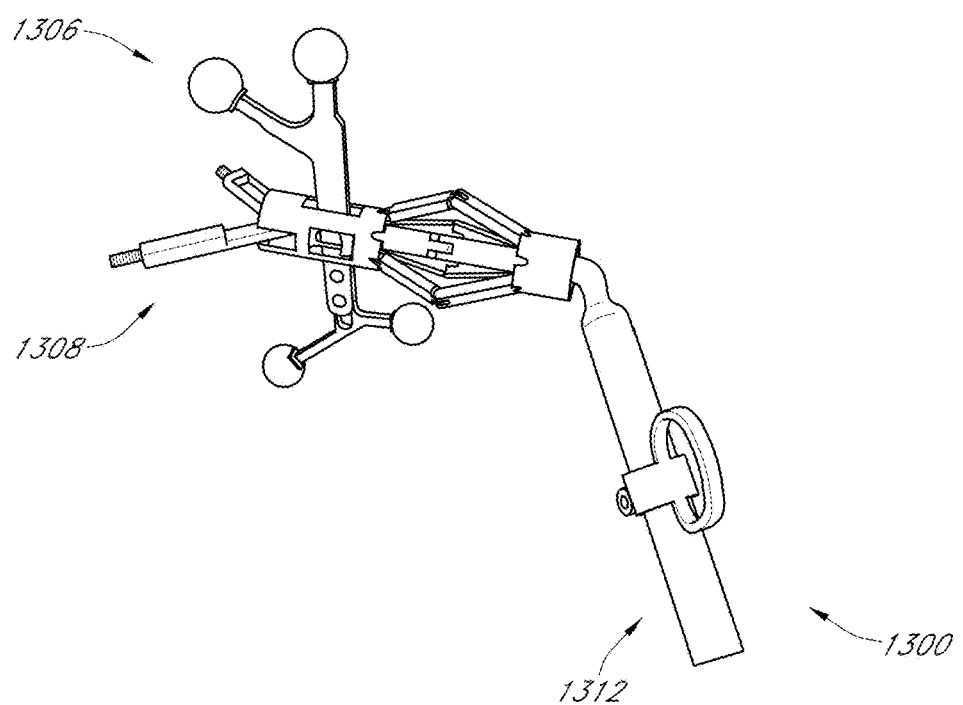

In one aspect of the disclosure, the emulator may be axially symmetric or axially asymmetric. FIGS. 13A and 13B illustrate an exemplary emulator 1300 that is axially symmetric. As shown in FIG. 13A, the emulator 1300 comprises a handle 1302, a connector 1304, and arms 1306 and 1308. The operator may hold the emulator 1300 by either the handle 1302 or the connector 1304 (as shown by the hand 1310 of the operator). Each of the arms 1306 and 1308 may comprise one or more branches 1307 and 1309, respectively. The branches of the arm may be positioned symmetrically with respect to the longitudinal axis of the arm (e.g., branches 1309 of the arm 1308) or asymmetrically with respect to the longitudinal axis of the arm (e.g., branches 1307 of the arm 1306). The branches 1307 and 1309 of each arm 1306 or 1308 may be positioned to be on the same plane. The plane formed by the branches 1307 and the plane formed by the branches 1309 may, for example, be perpendicular to each other. As shown in FIG. 13B, the connector 1304 may comprise a plurality of legs. The longitudinal length of the connector 1304 may be modified by adjusting the bending degree of bending of legs of the connector 1304. The connector 1304 and the handle 1302 may be connected by a joint such that the connecting angle between the connector 1304 and the handle 1302 may be adjusted based on different grip positions of the operator. The axially symmetric emulator 1300 may be beneficial because it can avoid an implication of mapping an operator grip roll angle (e.g., roll angle of the emulator 1300) to the instrument grip roll angle (e.g., roll angle of the medical device). In some aspects, the emulator may be symmetric with respect to one or more of the pitch, yaw, and roll axes.

Figure 14:
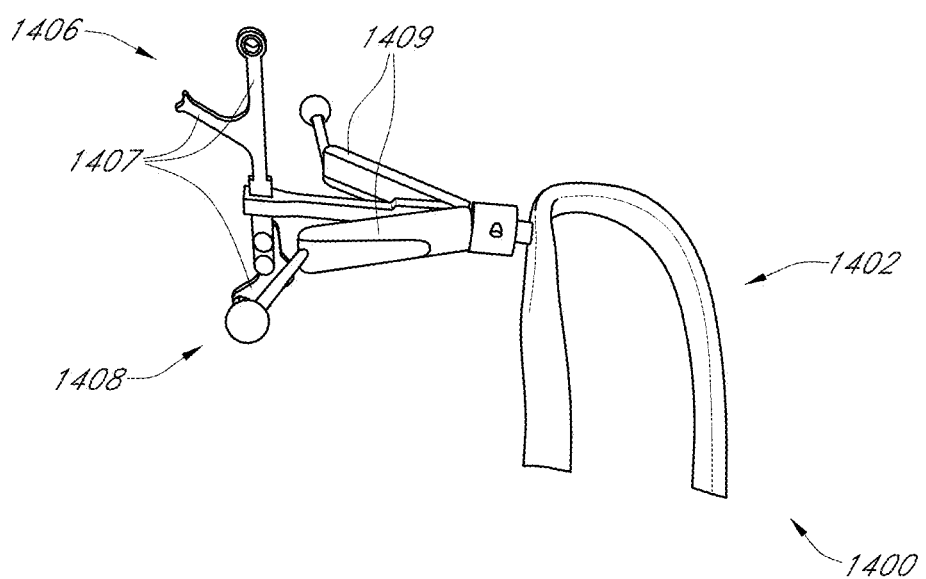
FIG. 14 illustrates an emulator, according to yet another embodiment.

FIG. 14 illustrates an exemplary emulator 1400 that is axially asymmetric. The emulator 1400 comprises a handle 1402 and arms 1406 and 1408. Each of the arms 1406 and 1408 may comprise one or more branches 1407 and 1409, respectively. The handle 1402 of the emulator is shaped to be axially asymmetric. When the non-axially symmetric emulator 1400 is used, an angular offset experienced by the operator (which is common in traditional manual medical devices that allow the device shaft to be rotated with respect to the handle) may be compensated for.

Figure 15:
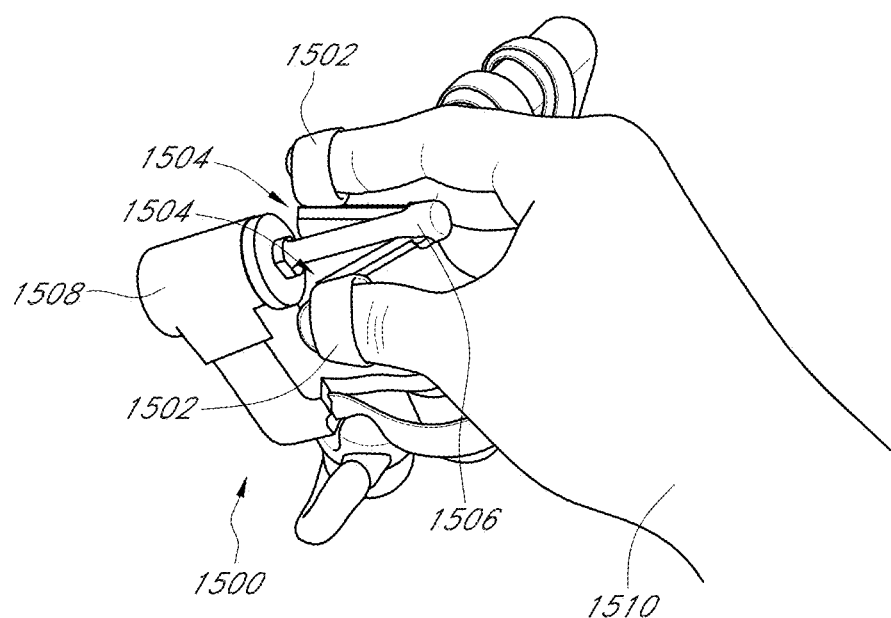
FIG. 15 illustrates an emulator, according to still another embodiment.

FIG. 15 illustrates an exemplary emulator 1500 that is axially asymmetric. The emulator 1500 comprises one or more rings 1502, one or more pinchers 1504, a rod 1506, and a support 1508. The one or more rings 1502 are configured to receive fingers of the operator (as shown by the hand 1510 of the operator). Each of the rings 1502 is connected to one of the pinchers 1504 and enables the operator to manipulate the pinchers 1504 when the operator inserts his/her fingers into the rings 1502. One or more pinchers 1504 are connected to the rod 1506, and the rod 1506 is mounted on the support 1508. Tips of the pinchers 1504 may be pushed toward the longitudinal axis of the rod 1506, and the movement of the pinchers 1504 may be tracked by one or more detectors (e.g., sensors inside the rod 1506). In some aspects, the emulator may be asymmetric with respect to one or more of the pitch, yaw, and roll axes.

In some aspects, the emulator 1500 may be used in conjunction with one or more medical devices that are configured to pinch or clamp or operate by a pinching movement of the operator, including but not limited to forceps, clamps, scissors, and vessel sealers. When the operator pushes the pinchers 1504 using his/her fingers toward the longitudinal axis of the rod 1506, the movement of the pinchers 1504 may be detected by the sensors, and the medical device may be operated or moved based on the movement of the pinchers 1504.

Implementing Systems and Terminology

Implementations disclosed herein provide systems, methods and apparatus for to robotically controlling a medical device. More specifically, implementations of the present disclosure relate to a system for reducing an alignment offset; a camera control system; and a system for a clutched roll.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods described herein may be stored as one or more instructions on a processor-readable or computer-readable medium. The term "computer-readable medium" refers to any available medium that can be accessed by a computer or processor. By way of example, and not limitation, such a medium may comprise random-access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present disclosure. Various modifications to these implementations will be readily apparent to those skilled in the art, and the generic principles defined herein may be applied to other implementations without departing from the scope of the present disclosure. For example, it will be appreciated that one of ordinary skill in the art will be able to employ a number of corresponding alternative and equivalent structural details. Thus, the present disclosure is not intended to be limited to the implementations shown herein but is to be accorded the widest scope consistent with the principles and novel features disclosed herein.

What is claimed is:

1. A system, comprising:
    an emulator configured to be held and operated in a free working space (FWS), the emulator representing a medical device at a target site;
    at least one detector configured to track the emulator within the FWS;
    at least one computer-readable memory having stored thereon executable instructions; and
    at least one processor in communication with the at least one computer-readable memory and configured to execute the instructions to cause the system to:
        determine an alignment offset between a location of the emulator and a location of the medical device;
        during a medical procedure, determine a first movement amount based on a signal from the at least one detector indicative of a first movement of the emulator within the FWS;
        adjust the first movement amount by a first adjustment value to iteratively lessen the alignment offset between the location of the emulator and the location of the medical device; and
        generate instructions to move the medical device based on the adjusted first movement amount, wherein the movement of the medical device by the adjusted first movement amount reduces the alignment offset between the location of the emulator and the location of the medical device.

2. The system of claim 1, wherein movement of the medical device by the adjusted first and second movement amounts eliminates the alignment offset between the location of the emulator and the location of the medical device.

3. A system, comprising:
    an emulator configured to be held and operated in a free working space (FWS), the emulator representing a medical device at a target site;
    at least one detector configured to track the emulator within the FWS;
    an imaging device configured to track the medical device at the target site;
    at least one computer-readable memory having stored thereon executable instructions; and
    at least one processor in communication with the at least one computer-readable memory and configured to execute the instructions to cause the system to:
        receive a signal from the at least one detector indicative of a translational movement of the emulator within the FWS; and
        generate instructions, based on the translational movement of the emulator, to move the imaging device within a plane defined by fixed pitch and yaw axes of the imaging device;
    wherein the translational movement of the emulator does not result in a translational movement of the medical device.

4. The system of claim 3, wherein the at least one processor is configured to execute the instructions to cause the system to:
    receive a signal from the at least one detector indicative of a rotational movement of the emulator within the FWS; and
    generate instructions, based on the rotational movement of the emulator, to rotate the medical device along a roll axis of the medical device.

5. The system of claim 4, wherein the rotational movement of the emulator does not result in a rotational movement of the imaging device.

6. A system, comprising:
    an emulator representing a medical device at a target site;
    a first set of one or more detectors configured to track the emulator;
    a second set of one or more detectors configured to track the medical device at the target site;
    at least one computer-readable memory having stored thereon executable instructions; and
    at least one processor in communication with the at least one computer-readable memory and configured to execute the instructions to cause the system to:
        receive, from the first set of one or more detectors, first data indicative of at least an orientation of the emulator, the first data comprising roll data, pitch data, and yaw data of the emulator;
        generate, based on a clutched user input, instructions to move the medical device based on the first data discounting the roll data of the emulator; and
        cause the medical device to move, without rotation about a roll axis of the medical device, based on the instructions.

7. The system of claim 6, wherein:
    the emulator is configured to be held and operated in a free working space (FWS); and
    the first set of one or more detectors is configured to track motion of the emulator in the FWS.

8. The system of claim 6, wherein:
    the emulator comprises a mechanical emulator; and the first set of one or more detectors is configured to track mechanical movement of the emulator.

9. The system of claim 6, wherein the discounting of the roll data of the emulator is based on decoupling a roll axis of the emulator from yaw and pitch axes of the emulator.

10. The system of claim 6, wherein the discounting of the roll data of the emulator is based on decoupling an absolute roll angle of the medical device from an absolute roll angle of the emulator.

11. The system of claim 6, wherein the emulator is symmetric with respect to a roll axis of the emulator.

12. The system of claim 6, wherein the emulator is asymmetric with respect to a roll axis of the emulator.

13. The system of claim 6, wherein the movement of the medical device based on the instructions facilitates adjustment of a roll axis of the emulator with respect to a roll axis of the medical device.

14. The system of claim 13, wherein:
the at least one processor is configured to execute the instructions to cause the system to receive, from the second set of one or more detectors, second data indicative of an orientation of the medical device at the target site, the second data comprising roll data, pitch data, and yaw data of the medical device; and
the alignment of the respective roll axes of the emulator and the medical device is based on the pitch and yaw data of the emulator and the pitch and yaw data of the medical device.

15. The system of claim 14, wherein the at least one processor is configured to execute the instructions to cause the system to:
receive, from the first set of one or more detectors, third data indicative of a translational movement of the emulator;
receive, from the second set of one or more detectors, fourth data indicative of a position of the medical device at the target site; and
generate instructions to move the medical device based on the third and fourth data.

16. The system of claim 1, wherein the first adjustment amount is a function of at least the first movement of the emulator, the alignment offset between the location of the emulator and the location of the medical device, and the first movement amount.

17. The system of claim 1, wherein the alignment offset between a location of the emulator and a location of the medical device can be expressed as $\theta'_n = \Sigma_i^j \varphi_i$;
wherein $\theta'_n$ is equal to the alignment offset, j is a number of iterations to reduce the alignment offset between a location of the emulator and a location of the medical device to zero, and $\varphi_i$ is the first adjustment amount.

18. The system of claim 1, wherein each of the plurality of adjustment values is associated with an iterative step and determined based on:
a relative misalignment between the location of the emulator and the location of the medical device at the iterative step,
a movement of the emulator at the iterative step, and
a corresponding movement of the medical device at the iterative step.

19. The system of claim 18, wherein each of the plurality of adjustment values is used to adjust the corresponding movement of the medical device based on the movement of the emulator to reduce the relative misalignment at each iterative step.

20. The system of claim 1, wherein after commanding movement of the medical device by the adjusted first movement amount to reduce the alignment offset while performing the medical procedure, the alignment offset is greater than zero.

* * * * *

UNITED STATES PATENT AND TRADEMARK OFFICE
CERTIFICATE OF CORRECTION

PATENT NO. : 11,037,464 B2
APPLICATION NO. : 15/657051
DATED : June 15, 2021
INVENTOR(S) : Ho et al.

It is certified that error appears in the above-identified patent and that said Letters Patent is hereby corrected as shown below:

In the Claims

Claim 1, Column 23, Line 53, please delete "device;" and insert --device, wherein the alignment offset can be expressed as a plurality of adjustment values configured to iteratively reduce the alignment offset, the plurality adjustment values comprising at least a first adjustment value and a second adjustment value;--;

Claim 1, Column 23, Line 55, please delete "on a signal" and insert --on a first signal--;

Claim 1, Column 23, Line 58, please delete "amount by a first" and insert --amount by the first--;

Claim 1, Column 23, Line 61, please delete "; and";

Claim 1, Column 23, please delete Lines 62 through 67, and insert
--command movement of the medical device by the adjusted first movement amount to reduce the alignment offset while performing the medical procedure;
determine a second movement amount based on a second signal from the at least one detector indicative of a second movement of the emulator within the FWS;
adjust the second movement amount by the second adjustment value to further iteratively lessen the alignment offset between the location of the emulator and the location of the medical device during the medical procedure; and
command movement of the medical device by the adjusted second movement amount to further reduce the alignment offset while continuing to perform the medical procedure.--.

Signed and Sealed this
Twenty-eighth Day of February, 2023

Katherine Kelly Vidal
*Director of the United States Patent and Trademark Office*